US008563548B2

(12) United States Patent
Marchal et al.

(10) Patent No.: US 8,563,548 B2
(45) Date of Patent: Oct. 22, 2013

(54) METHYLENE FURANONE DERIVATIVES AND USE OF SAID DERIVATIVES AS A PHOTOPROTECTING OR ANTIOXIDANT OR DEPIGMENTATION AGENT IN COSMETIC OR DERMATOLOGICAL COMPOSITIONS

(75) Inventors: Estelle Marchal, Valleroy (FR); Philippe Uriac, Pace (FR); Yves Brunel, Marssac-sur-tarn (FR); Stëphane Poigny, Saubens (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 128 days.

(21) Appl. No.: 13/120,822

(22) PCT Filed: Sep. 25, 2009

(86) PCT No.: PCT/EP2009/062476
§ 371 (c)(1),
(2), (4) Date: Mar. 24, 2011

(87) PCT Pub. No.: WO2010/034827
PCT Pub. Date: Apr. 1, 2010

(65) Prior Publication Data
US 2011/0184059 A1     Jul. 28, 2011

(30) Foreign Application Priority Data
Sep. 25, 2008   (FR) .................................. 08 56441

(51) Int. Cl.
*A61K 31/536*   (2006.01)
*C07D 265/34*   (2006.01)

(52) U.S. Cl.
USPC ....................... 514/230.5; 544/105

(58) Field of Classification Search
USPC ................ 514/471, 230.5; 549/321; 544/105
See application file for complete search history.

(56) References Cited

U.S. PATENT DOCUMENTS 6,258,963 B1   7/2001   Koch et al.

FOREIGN PATENT DOCUMENTS

WO   WO 2008/040097 A1   4/2008

OTHER PUBLICATIONS

Rossi, et al., Tetrahed. Let, (2000), vol. 41(27), pp. 5281-5286.*
Antonioletti, et al., Tetrahed. (1984), vol. 40(19), pp. 3805-3808.*
Biggerstaff et al., J. Org. Chem. (1967), vol. 32(8), pp. 2621-2613.*
Srogl et al., Collection of Czechoslovak Chem. Comm. (1968), vol. 33(6), pp. 1958-1962.*
King, Med. Chem., Principle and Practice (1994), pp. 206-208.*

Antonioletti et al., "A New Synthesis of 5-Methylene-2(5H)-Furanone Derivatives", Tetrahedron, vol. 40, No. 19, pp. 3805-3808, 1984, XP002523883.
Boukouvalas et al., "Facile Access to 4-Aryl-2(5H)-furanones by Suzuki Cross Coupling: Efficient Synthesis of Rubrolides C and E", Tetrahedron Letters, vol. 39, pp. 7665-7668, 1998.
Chellar et al., "Condensation of p-substituted 3-aryl-2-butenolides with aromatic and heterocyclic aldehydes", CAPLUS Database Accession No. 1986:109384, 1983, XP002523888.
French Preliminary Search Report, dated Apr. 16, 2009, for French Application No. 0856441.
International Search Report, dated Oct. 27, 2009, for Application No. PCT/EP2009/062476.
Kar et al., "A Facile Synthesis of Rubrolide E1", Synthesis, No. 14, pp. 2284-2286, 2005, XP002523884 (Published online Jul. 13, 2005).
Manny et al., "Reinvestigation of the Sulfuric Acid-Catalysed Cyclisation of Brominated 2-Alkyllevulinic Acids to 3-Alkyl-5-methylene-2(5H)-furanones", Tetrahedron, vol. 53, No. 46, pp. 15813-15826, 1997.
Prim et al., "Synthesis and stereochemistry of β-aryl-β-haloacroleins: useful intermediates for the preparation of (Z) and (E)-2-en-4-yne-carbaldehydes and for the synthesis of rubrolides", J. Chem. Soc., Perkin Trans. 2, pp. 1175-1180, 1999, XP002523886.
Rossi et al., "Palladium-catalyzed synthesis of stereodefined 3-[(1,1-unsymmetrically disubstituted)methylidene]isobenzofuran-1(3H)-ones and stereodefined 5-[(1,1-unsymmetrically disubstituted)methylidene]furan-2(5H)-ones", Tetrahedron Letters, vol. 41, pp. 5281-5286, 2000.
Saalfrank et al., "Convenient Synthesis of 5-Alkylidene-2(5H)-Furanones, 2(5H)-Furanones and 2-Ethoxyfurans", Tetrahedron, vol. 44, No. 16, pp. 5095-5100, 1988, XP002523885.
Sidky et al., "Organophosphorus compounds, XXX, The Reaction of fluorenylidenetriphenylphosphorane with maleic, phthalic and thiophthalic anhydrides", CAPLUS Database Accession No. 1980:639115, 1980, XP002550711.
Sorg et al., "A Novel Access to γ-Alkylidenbutenolides: Sequential Stille Couplings of Dibromomethylenebutenolides", Synlett, No. 2, pp. 321-325, 2004 (Published online Dec. 16, 2003).
Wu et al., "Palladium-Catalyzed Cross-Coupling Reactions of 4-Tosyl-2(5H)-furanone with Boronic Acids: A Facile and Efficient Route to Generate 4-Substituted 2(5H)-Furanones", J. Org. Chem., vol. 68, No. 2, pp. 670-673, 2003, XP002523887 (Published online Dec. 14, 2002).

* cited by examiner

*Primary Examiner* — Taofiq A Solola
(74) *Attorney, Agent, or Firm* — Birch, Stewart, Kolasch & Birch, LLP.

(57) ABSTRACT

The present invention relates to methylene furanone derivatives as well as the use thereof as a protective, antioxidant, or depigmentation agent in cosmetic or dermatological compositions. The invention also relates to a method for preparing said derivatives involving a Suzuki-Miyaura coupling reaction from corresponding dibromofuranone derivatives. The invention also relates to a method of preparation involving a coupling reaction of 2-methoxy-furan derivatives with a ketone followed by dehydration.

11 Claims, 3 Drawing Sheets

METHYLENE FURANONE DERIVATIVES AND USE OF SAID DERIVATIVES AS A PHOTOPROTECTING OR ANTIOXIDANT OR DEPIGMENTATION AGENT IN COSMETIC OR DERMATOLOGICAL COMPOSITIONS

BACKGROUND OF THE INVENTION

The present invention relates to methylene furanone derivatives, the synthesis thereof, as well as the use thereof as a photoprotecting or antioxidant or depigmentation agent in cosmetic or dermatological compositions.

Methylene furanone derivatives are molecules that are very abundant in nature. They are found, for example, in the components of celery odour in the form of alkylidene-benzofuranone (a). They are also represented in lichens by pulvinic acid (b), which is responsible for their yellow pigmentation. They are also known to have a wide variety of biological activities. Thus, protoanemonin (c) has antimicrobial and antifungal properties, rubrolide A (d) has antibacterial properties and dihydroxerulin (e) inhibits cholesterol synthesis.

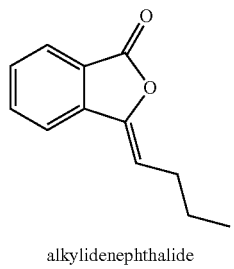

alkylidenephthalide a

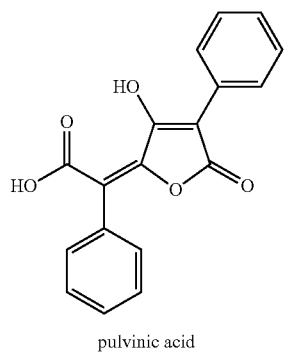

pulvinic acid b

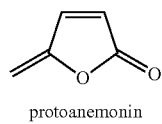

protoanemonin c

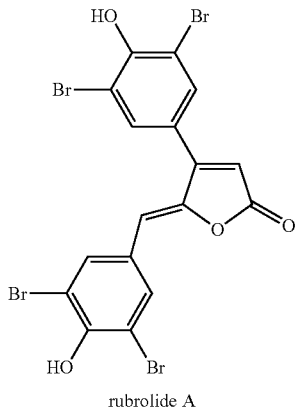

rubrolide A d

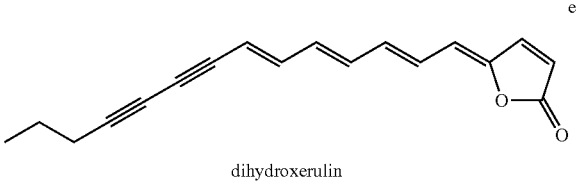

dihydroxerulin e

BRIEF SUMMARY OF THE INVENTION

The present invention relates to methylene furanone derivatives of general formula (I)

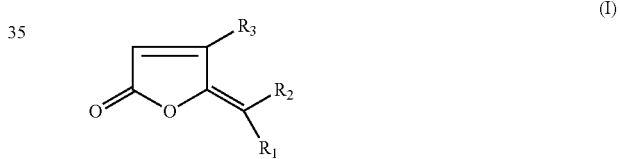

(I)

in their (E) or (Z) isomer forms, pure or in mixture,
wherein $R_3$ represents hydrogen and wherein:
$R_1$ and $R_2$ are identical and represent
a phenyl radical substituted by one or more of the following radicals
($C_{1-5}$) alkyl, ($C_{1-4}$) alkoxy,
hydroxy,
methylthio,
halogen, or
an amino group optionally substituted by a ($C_{1-4}$) alkyl or ($C_{1-4}$) alkoxycarbonyl radical,
a thiophenyl radical,
a thionaphthenyl radical,
a thiazolyl radical,
a pyridinyl radical,
a benzomorpholinyl radical,
a naphthyl radical
and
on the condition, however, that $R_1$ and $R_2$ do not simultaneously represent a paramethoxyphenyl radical.

The invention further relates to methylene furanone derivatives of general formula (I), in their (E) or (Z) isomer forms, pure or in mixture, wherein:
$R_3$ represents hydrogen
$R_1$ and $R_2$ are identical and represent a phenyl radical substituted by one or more of the following radicals
$(C_{1-4})$ alkoxy,
hydroxy,
a thiophenyl radical,
and on the condition, however, that $R_1$ and $R_2$ do not simultaneously represent a paramethoxyphenyl radical.

The invention further relates to methylene furanone derivatives of general formula (I), in their (E) or (Z) isomer forms, pure or in mixture, wherein:
$R_3$ represents hydrogen
$R_1$ and $R_2$ are identical and represent
a phenyl radical substituted by one or more hydroxy radicals More particularly, the invention relates to the following compounds, methylene furanone derivatives of general formula (I), in their (E) or (Z) isomer forms, pure or in mixture, selected among:
5-(bis(3,4-dimethoxyphenyl)methylene)furan-2(5H)-one;
5-(dithiophene-3-ylmethylene)furan-2(5H)-one;
5-bis(tert-butyl-4-hydroxyphenylcarbamate)furan-2(5H)-one;
(Z)-5-(3,4-dimethoxyphenylmethylene)-4-(3,4-dimethoxyphenylmethylene)furan-2(5H)-one;
(Z)-5-(phenylthiophene-3-ylmethylene)furan-2(5H)-one;
5-(bis(2-fluorophenyl)methylene)furan-2(5H)-one;
5-(bis(4-(methylthio)phenyl)methylene)furan-2(5H)-one;
5-(bis(4-(dimethylamino)phenyl)methylene)furan-2(5H)-one;
5-(bis(4-methyl-3,4-dihydro-2H-benzo[b][1,4]oxazin-7-yl)methylene)furan-2(5H)-one;
5-(dithiazol-2-ylmethylene)furan-2(5H)-one;
5-(bis(4-fluorophenyl)methylene)furan-2(5H)-one;
5-(bis(4-hydroxy-3,5-dimethylphenyl)methylene)furan-2(5H)-one;
5-(bis(3,4,5-trihydroxyphenyl)methylene)furan-2(5H)-one;
5-(bis(3,4-dihydroxyphenyl)methylene)furan-2(5H)-one;
5-(bis(4-hydroxy-3-methoxyphenyl)methylene)furan-2(5H)-one;
5-(bis(4-hydroxy-3,5-dimethoxyphenyl)methylene)furan-2(5H)-one;
5-(bis(4-hydroxyphenyl)methylene)furan-2(5H)-one;
5-(bis(2,4-dimethoxyphenyl)methylene)furan-2(5H)-one;
5-(bis(2,4-dihydroxyphenyl)methylene)furan-2(5H)-one.

The invention further relates to derivatives of general formula (I):

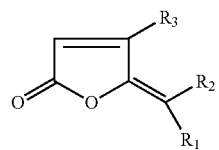

(I)

in their (E) or (Z) isomer forms, pure or in mixture,
wherein one of the radicals $R_1$ and $R_3$ necessarily represent hydrogen,
wherein $R_1$, $R_2$, $R_3$ are identical or different and represent:
a phenyl radical optionally substituted by one or more of the following radicals
$(C_{1-5})$ alkyl, $(C_{1-4})$ alkoxy,
hydroxy,
methylthio,
halogen, or
an amino group optionally substituted by a $(C_{1-4})$ alkyl or $(C_{1-4})$ alkoxycarbonyl radical,
a thiophenyl radical,
a thionaphthenyl radical,
a thiazolyl radical,
a pyridinyl radical,
a benzomorpholinyl radical,
a naphthyl radical.
$R_1$ and $R_2$ are bonded together and represent a fluorenyl radical
for the use thereof as a photoprotecting or antioxidant agent.

More particularly, the invention relates to derivatives of general formula (I), in their (E) or (Z) isomer forms, pure or in mixture, wherein:
$R_3$ represents hydrogen, and
$R_1$ and $R_2$ are identical or different and represent
a phenyl radical optionally substituted by one or more of the following radicals
$(C_{1-5})$ alkyl, $(C_{1-4})$ alkoxy,
hydroxy,
methylthio,
halogen, or
an amino group optionally substituted by a $(C_{1-4})$ alkyl or $(C_{1-4})$ alkoxycarbonyl radical,
a thiophenyl radical,
a thionaphthenyl radical,
a thiazolyl radical,
a pyridinyl radical,
a benzomorpholinyl radical,
a naphthyl radical.
$R_1$ and $R_2$ are bonded together and represent a fluorenyl radical
for the use thereof as a photoprotecting or antioxidant agent.

The invention further relates to dermocosmetic or dermatological compositions containing a photoprotecting or antioxidant agent such as defined above in combination with a cosmetically or pharmaceutically acceptable excipient.

The invention further relates to derivatives of general formula (I), in their (E) or (Z) isomer forms, pure or in mixture, wherein:
$R_3$ represents hydrogen
$R_1$ and $R_2$ are identical and represent
a phenyl radical substituted by one or more hydroxy radicals
for the use thereof as a depigmentation agent.

The invention relates to dermocosmetic or dermatological compositions containing a depigmentation agent such as defined above in combination with a cosmetically or pharmaceutically acceptable excipient.

DETAILED DESCRIPTION OF THE INVENTION

Figure 1:
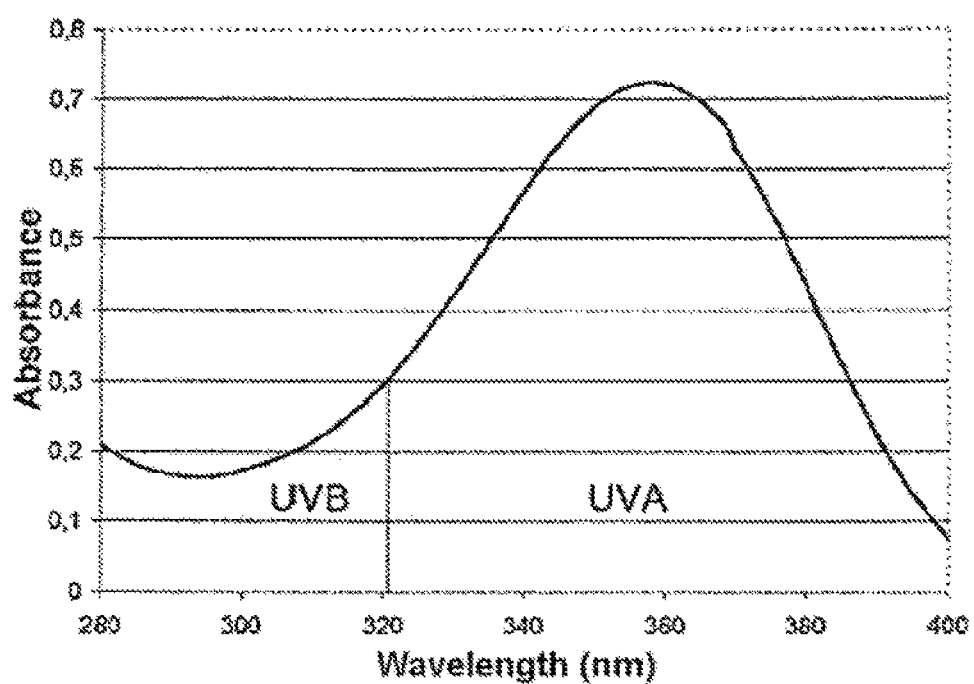
FIG. 1 depicts a graph that illustrates molecules absorbing only UVA (Strict UVA Category)

The compounds of general formula (I) according to the invention can be prepared according to the synthesis schemes below.

1. Via Suzuki-Miyaura Coupling

In order to obtain methylene furanone derivatives 4 and 5 the synthesis strategy selected consists in transforming 3,5-dibromolevulinic acid 1 (Manny, A. J.; Kjelleberg, S.; Kumar, N.; de Nys, R.; Read, R. W.; Steinberg, P., *Tetrahedron* 1997, 53, 158813-15826) into dibromofuranones 2 and 3. Their formation is dependent on the conditions used: at 110° C. in concentrated sulphuric acid 2 will be obtained predominantly, and 3 by treatment in oleum at 65° C.

cially available. On the other hand, these acids in situ form cyclic trimers (boroxines), and in general they should be used in excess.

Boronic esters can be used in stoichiometric quantity. Alkyl boranes are also commonly used. The catalysts most commonly used in Suzuki-Miyaura coupling are $Pd(PPh_3)_4$, $Pd(OAc)_2$, $Pd(dba)_2$, $Pd_2(dba)_3$ and $PdCl_2$.

Preparation of Dibrominated Lactones 2 and 3

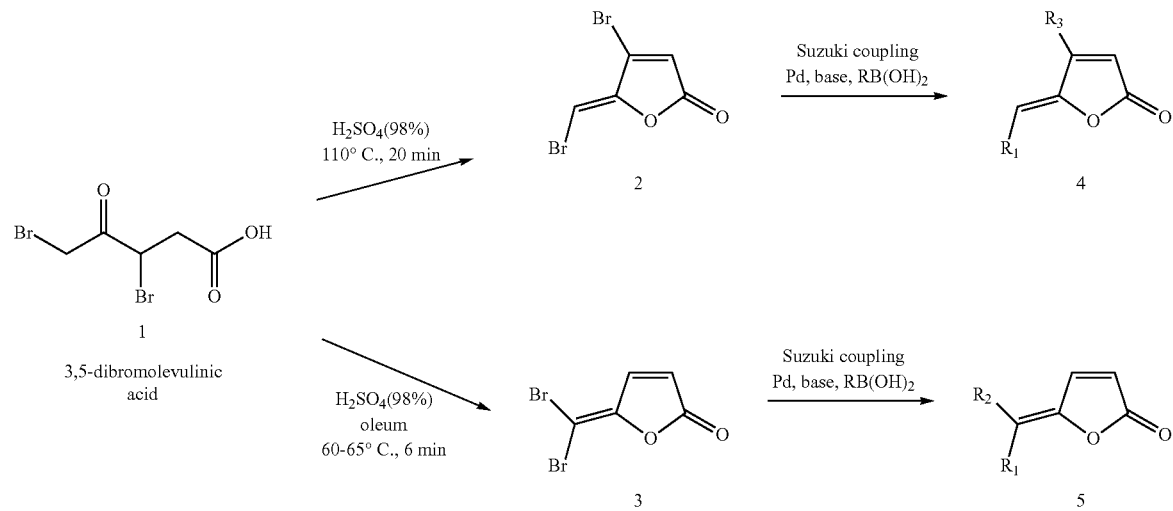

Then bromine atoms are substituted by aromatic groups (in a concomitant or sequential manner) by Suzuki-Miyaura coupling.

Suzuki-Miyaura coupling catalyses the formation of carbon-carbon bonds between an organoboron compound (carrying an sp, $sp^2$ or $sp^3$ carbon) and various electrophiles, catalysed by palladium complexes, in the presence of a base.

The choice of bases depends on the organoboron species and the partner electrophile used. They are principally mineral bases, such as $Na_2CO_3$, NaOH, $K_2CO_3$, $NaHCO_3$, $K_3PO_4$, NaOAc, CsF, etc.

The boronic acids most commonly employed are not very sensitive to air. Moreover, a very large number are commer- The synthesis of bromolactones 2 and 3 is carried out from 3,5-dibromolevulinic acid 1, itself obtained by bromination of levulinic acid. In the presence of hot concentrated sulphuric acid, dibromomethylenefuranone 2 is predominantly obtained with a yield of 35%. The preparation of dibromomethylenefuranone 3 requires the presence of a mixture of oleum and concentrated sulphuric acid. The yield of this reaction is only 20%. These poor yields can be explained by the drastic conditions used and the average stability of these brominated compounds. It is to date the only method known for their synthesis.

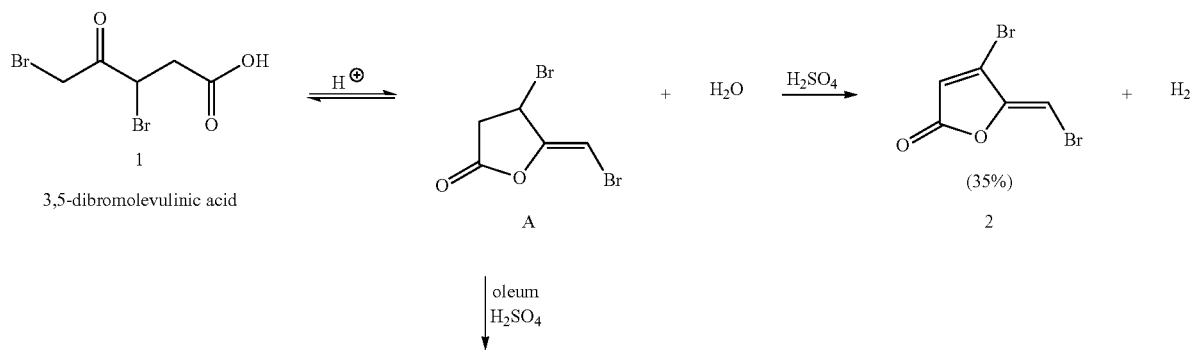

-continued

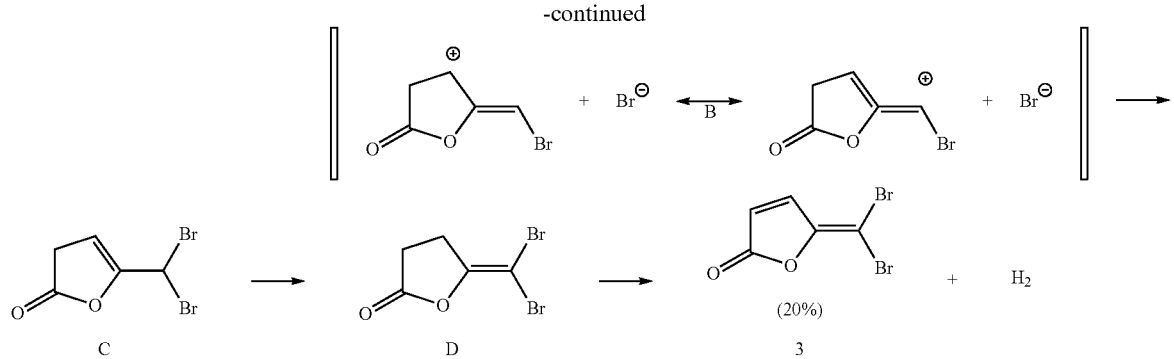

The first common intermediate A of this reaction results from cyclisation of 3,5-dibromolevulinic acid. The concentrated sulphuric acid pathway can then give substrate 2 by dehydrogenation. For the second pathway, the presence of oleum enables the formation of allylic carbocation B and thus causes the transposition of bromine (intermediate C). Next, migration of the double bond gives compound D which, under the influence of the oxidising character of sulphuric acid, leads to dibromomethylenefuranone 3.

Disubstitution of Brominated Lactones 2 and 3 by Suzuki-Miyaura Coupling

The implementation of Suzuki-Miyaura coupling on brominated furanones 2 and 3 made it possible to produce two families of methylene furanone derivatives, one disubstituted by identical aromatics and the other disubstituted by different aromatics.

Case of Methylene Furanone Derivatives 4 and 5, Substituted by Identical Aromatics.

Two methods can be applied to carry out these couplings:

Method A
  $ArB(OH)_3$, 3 eq
  $Pd(PPh_3)_4$, 3 mol %
  $K_2CO_3$, 3 eq
  Toluene/$H_2O$/EtOH
  100° C., 4 h Method B
  $ArB(OH)_3$, 3 eq
  $Pd(OAc)_2$, 1 mol %
  S-Phos 2-10, 2 mol %
  $K_3PO_4$, 3 eq
  Toluene, 100° C., 4 h

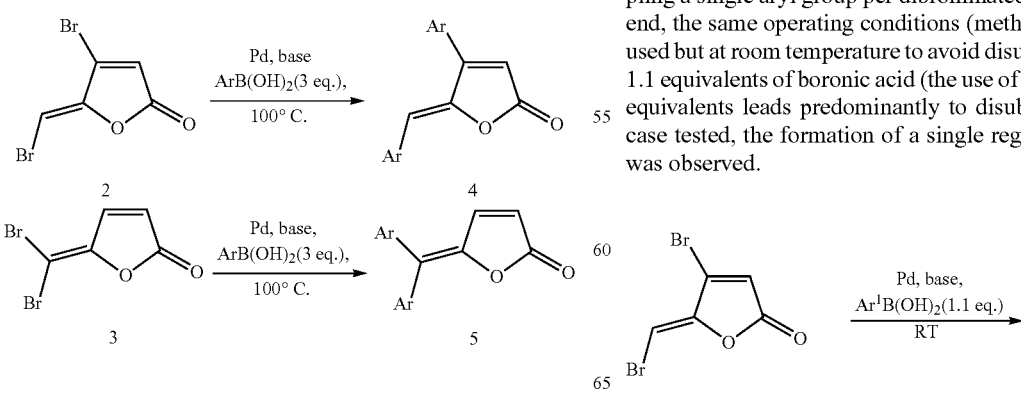

The two methods employed were compared; the results are presented below.

| Lactones | Substituents | Method A yields (%) | Method B yields (%) |
|---|---|---|---|
| 4a | $C_6H_5$— | 74 | 55 |
| 4b | 3-thienyl- | 52 | 72 |
| 4c | naphthyl- | 63 | 35 |
| 4d | 3-MeO, 4-MeO—$C_6H_3$— | 47 | —[a] |
| 4e | p-NBoc-$C_6H_4$— | 52 | 25 |
| 4f | o-F—$C_6H_5$— | — | 71 |
| 5a | $C_6H_5$— | 62 | 83 |
| 5b | 3-thienyl- | 66 | 40 |
| 5c | naphthyl- | 57 | 88 |
| 5d | 3-MeO, 4-MeO—$C_6H_3$— | 50 | 25 |
| 5e | p-NBoc-$C_6H_4$— | — | 86 |
| 5f | o-F—$C_6H_5$— | — | 80 |
| 5h | 3,4,5-tri-MeO—$C_6H_2$— | 70 | — |
| 5j | 4-MeS—$C_6H_4$— | 60 | — |

[a] Absence of reaction.

Yields obtained for couplings on brominated lactones 2 and 3.

Case of Methylene Furanone Derivatives 4 and 5 Substituted by Different Aromatics Regioselective Monosubstitution of Brominated Lactones 2 and 3 by Suzuki-Miyaura Coupling The regioselectivity of this reaction was studied by coupling a single aryl group per dibrominated derivative. To this end, the same operating conditions (methods A and B) were used but at room temperature to avoid disubstitution and with 1.1 equivalents of boronic acid (the use of a higher number of equivalents leads predominantly to disubstitution). In each case tested, the formation of a single regioisomer (6 and 7) was observed.

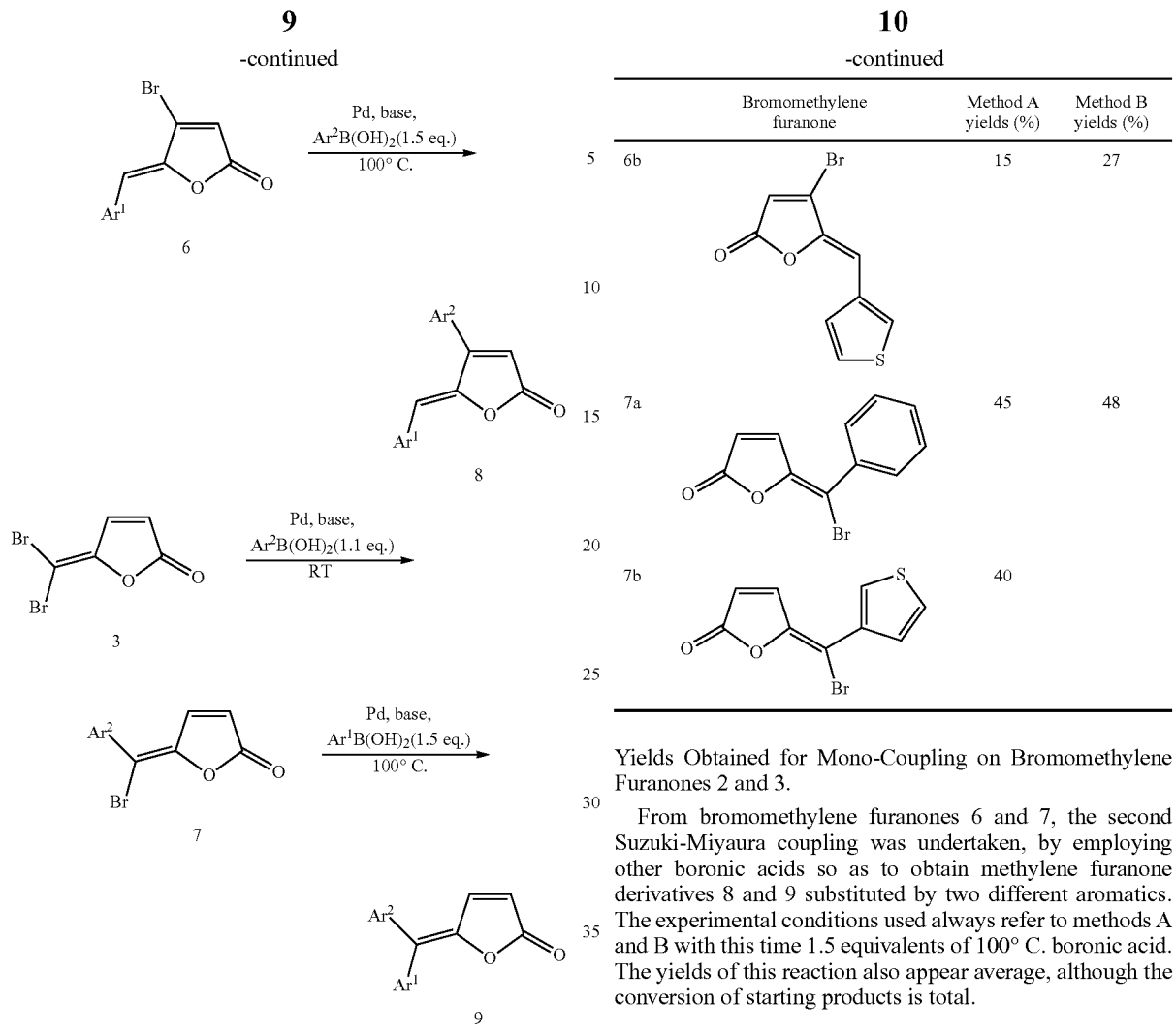

Synthesis of Methylene Furanone Derivatives by Successive Monosubstitutions.

The yields of this reaction are low with averages that seem predominantly due to degradation of the starting product in the reaction medium. Indeed, in most cases only traces of it remain at the end of the reaction. Moreover, the formation of disubstituted secondary compounds is very low, except for 6b (methods A and B) and 6a (method B). This reaction thus appears rather delicate.

Yields Obtained for Mono-Coupling on Bromomethylene Furanones 2 and 3.

From bromomethylene furanones 6 and 7, the second Suzuki-Miyaura coupling was undertaken, by employing other boronic acids so as to obtain methylene furanone derivatives 8 and 9 substituted by two different aromatics. The experimental conditions used always refer to methods A and B with this time 1.5 equivalents of 100° C. boronic acid. The yields of this reaction also appear average, although the conversion of starting products is total.

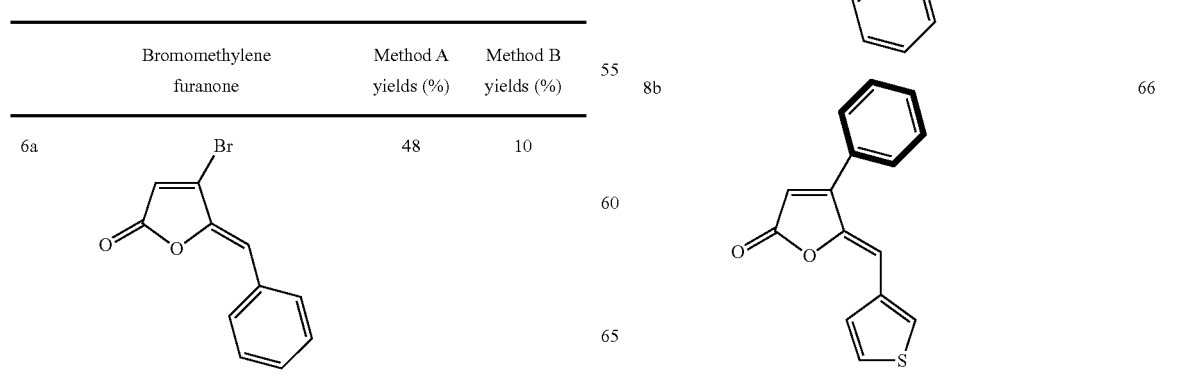

| Methylene furanone derivatives | Method A yields (%) | Method B yields (%) |
|---|---|---|
| 9a | 48 | |
| 9b | 42 | | a: The aromatics in bold result from the second coupling.

Structural Determination by NMR

In order to determine the structure of the compounds resulting from regioselective mono-coupling, NMR was used to study a compound of each series: 4- and 5-disubstituted furanone series: compound 6a, and 5-gem-disubstituted furanone series: compound 9b.

4- and 5-Disubstituted Furanone Series: Compound 6a

The 2D proton-carbon HMBC study made it possible to easily determine the regiochemistry of the reaction during the first organometallic coupling and confirms that it is position 6 that was substituted.

5-Disubstituted Furanone Series: Compound 9b

First, the NMR data of compound 7a was compared with the data in the literature (Sorg, A. Siegel, K.; Brückner, R. *Synlett* 2004, 2, 231-325.). The latter indicate the presence of Z stereoisomer. For compound 9b a NOESY study was undertaken. Compound 9b results from a first coupling with thiopheneboronic acid, then coupling with phenylboronic acid. A correlation is clearly observed between proton $H_4$ and the thiophene protons, which confirms the Z stereochemistry of the compound resulting from the first coupling.

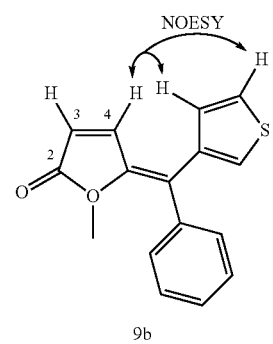

9b

2—Via 2-Methoxy-furan

According to the literature, there are two steps: adding the lithium of 2-methoxyfurane on the ketone (*JACS*, 1986, 7055 and *Synth. Comm.*, 2008, 212) then dehydration of the alcohol obtained (*JACS*, 1986, 7055):

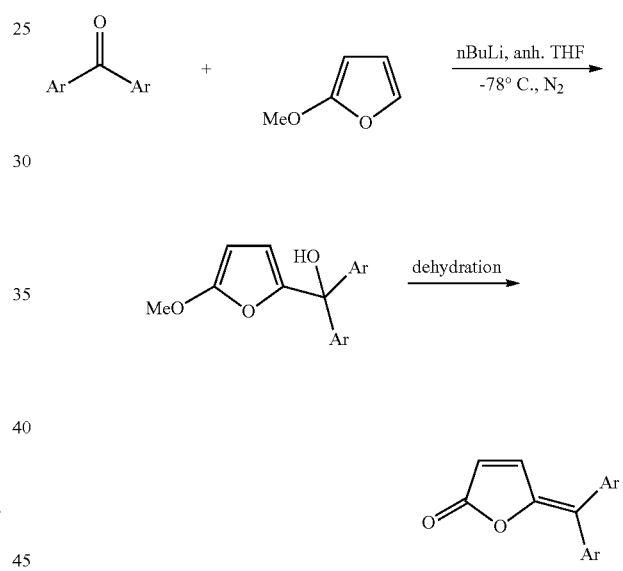

However, dehydration is sometimes spontaneous and the olefin is then directly isolated without passing by the alcohol.

The example known in the literature is as follows (*JACS*, 1986, 7055):

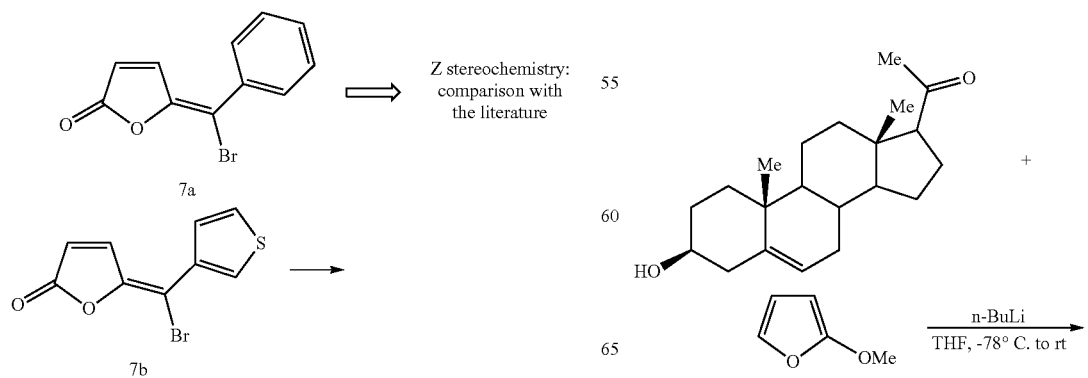

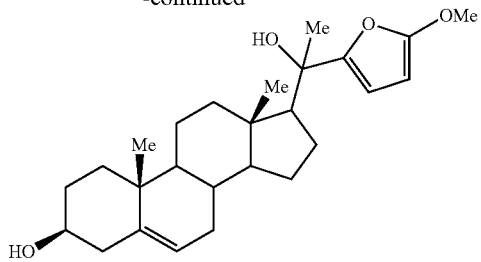

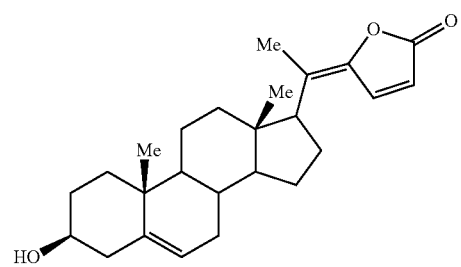

From 3',3',4',4'-tetramethoxybenzophenone (10)

Starting ketone 10 is obtained according to the conditions described in the literature (*Eur. J. Org. Chem.*, 2004, 2381).

Ketone 10 was then used in the following reaction to directly give olefin 5d. Compound 5d was treated with boron tribromide (*Tet.*, 2005, 2055) to give phenolic derivative 5g (73%) in the form of a green solid.

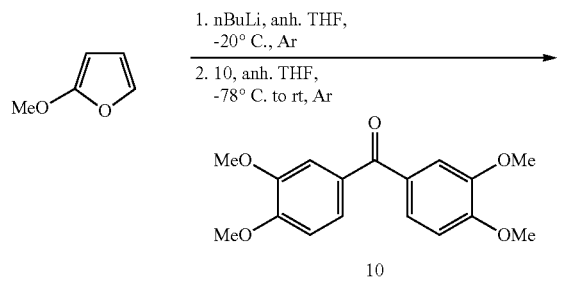

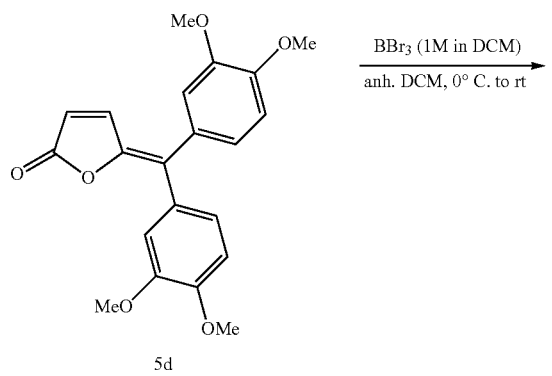

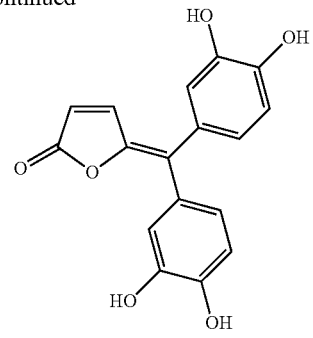

From di-2-thienylketone:

The compound was obtained in a single step with yields of 52% from 2-methoxyfurane and di-2-thienyl ketone.

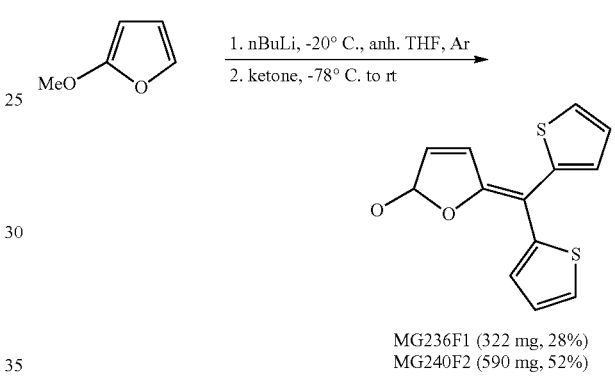

From di-3-thienylketone:

Compound 5b (34%) was obtained in a single step from 2-methoxyfurane and di-3-thienyl ketone prepared according to the procedure described (*Synthesis*, 2000, 1253).

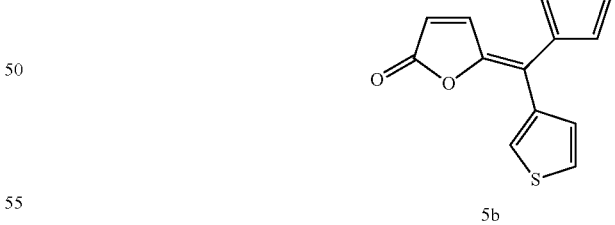

The present invention thus further relates to a method for preparing methylene furanone derivatives of general formula (I), in their (E) or (Z) isomer forms, pure or in mixture:
wherein necessarily $R_3$ represents hydrogen,
wherein $R_1$ and $R_2$ are identical and represent:
  a phenyl radical substituted by one or more of the following radicals
    ($C_{1-5}$) alkyl, ($C_{1-4}$) alkoxy,
    hydroxy,
    methylthio, halogen, or
an amino group optionally substituted by a $(C_{1-4})$ alkyl or $(C_{1-4})$ alkoxycarbonyl radical,
a thiophenyl radical,
a thionaphthenyl radical,
a thiazolyl radical,
a pyridinyl radical
a benzomorpholinyl radical,
a naphthyl radical, and on the condition, however, that $R_1$ and $R_2$ do not simultaneously represent a paramethoxyphenyl radical, characterised in that it involves a Suzuki-Miyaura coupling reaction from dibromofuranone derivatives of general formula (II), in their (E) or (Z) isomer forms, pure or in mixture:

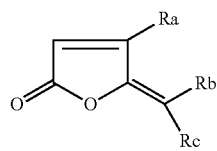

wherein

Ra represents hydrogen and Rb and Rc represent a bromo radical, or

Rb represents hydrogen and Ra and Rc represent a bromo radical.

The present invention further relates to a method for the synthesis of methylene furanone derivatives of general formula (I), in their (E) or (Z) isomer forms, pure or in mixture:

wherein necessarily $R_3$ represents hydrogen, wherein $R_1$ and $R_2$ are identical and represent:
a phenyl radical substituted by one or more of the following radicals
$(C_{1-5})$ alkyl, $(C_{1-4})$ alkoxy,
hydroxy,
methylthio,
halogen, or
an amino group optionally substituted by a $(C_{1-4})$ alkyl or $(C_{1-4})$ alkoxycarbonyl radical,
a thiophenyl radical,
a thionaphthenyl radical,
a thiazolyl radical,
a pyridinyl radical
a benzomorpholinyl radical,
a naphthyl radical, and on the condition, however, that $R_1$ and $R_2$ do not simultaneously represent a paramethoxyphenyl radical, characterised in that it involves a coupling reaction of 2-methoxyfurane with a ketone followed by dehydration in situ or with a dehydration agent.

The present invention will be described below in more detail in the light of the examples of preparation indicated below as non-restrictive illustrations.

Synthesis of Intermediates 3,5-Dibromolevulinic acid (1)

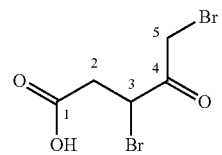

Levulinic acid (12 g, 0.103 mol) is dissolved in chloroform (60 ml). $Br_2$ (27.7 ml, 0.226 mol) is added very slowly (2.5 h) at room temperature. Chloroform (80 ml) is added to the reaction medium to help stirring. HBr is driven out by a stream of nitrogen.

One hour and thirty minutes after adding bromine, the reaction medium is cooled to 0° C. The precipitate is filtered and washed with chloroform to give a white solid with a yield of 53% (15 g, 0.054 mol).

MP: 110-112° C.; TLC: (hexane/MeOH 50/50) $R_f$=0.25; $^1$H-NMR (CDCl$_3$): δ=3.05 (dd, 1H, J=17.8, 5.9 Hz, H$_2$), 3.38 (dd, 1H, J=17.8, 8.5 Hz, H$_2$), 4.17 (d, 1H, J=13.1 Hz, H$_5$), 4.38 (d, 1H, J=13.1 Hz, H$_5$), 5.01 (dd, 1H, J=8.5, 5.9 Hz, H$_3$) ppm.

4-Bromo-5-(bromomethylene)furan-2(5H)-one (2)

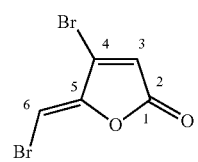

A suspension of 3,5-bromolevulinic acid 1 (1.00 g, 3.65 mmol) in sulphuric acid (98%, 5 ml) is stirred at 105° C. for 20 min. Once returned to room temperature, the brown solution obtained is poured on ice, and extracted with $CH_2Cl_2$ (2 times, 30 ml). The combined organic phases are washed with NaCl saturated water solution and dried on $Na_2SO_4$. The solvents are evaporated with a rotary evaporator. The brown residue obtained is chromatographed on silica and eluted with a pentane/Et$_2$O mixture (90/10). Cream-white crystals are obtained with a 35% yield (0.33 g, 128 mmol).

$R_f$=0.58 (Et$_2$O/pentane, 10:90), MP 97-98° C. $^1$H-NMR (CDCl$_3$): δ=6.50 (s, 1H, 3-H), 6.42 (s, 1H, 6-H) ppm. $^{13}$C-NMR (CDCl$_3$): δ=93.7 (C-6), 121.0 (C-3), 135.3 (C-4), 165.4 (C-2) ppm. IR (KBr): υ=3129, 3080, 1809 (C═O), 1771

(C=O), 1642, 1553, 1552, 1438, 1311, 1247, 1167, 1118, 1085, 1006, 977, 928, 904, 845, 812, 788, 754, 718, 646, 538 cm$^{-1}$.

5-(Dibromomethylene)furan-2(5H) one (3)

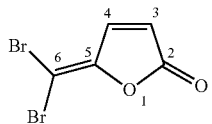

To 3,5-bromolevulinic acid 1 (2.37 g, 8.65 mmol) is added a mixture of oleum (fuming sulphuric acid, 65% $SO_3$, 4 ml) and sulphuric acid (98%, 2 ml) at room temperature. After heating at 60-65° C. for 6 min, the reaction medium is returned to room temperature and poured on 100 g of ice. A yellow precipitate appears and the mixture is extracted with $CH_2Cl_2$ (6 times, 50 ml). The combined organic phases are washed with NaCl saturated water solution, and dried on $Na_2SO_4$. The solvent is evaporated with a rotary evaporator, and the brown residue obtained is chromatographed on silica with a pentane/$Et_2O$ mixture (75/25) as eluent. White crystals are obtained with a yield of 31% (0.29 g, 1.13 mmol).

$R_f$=0.64 ($Et_2O$/pentane, 25:75), MP 133-135° C. $^1$H-NMR ($CDCl_3$): δ=6.42 (d, 1H, J=5.4 Hz, 3-H). 7.68 (d, 1H, J=5.6 Hz, 4-H) ppm. IR (KBr): υ=3128, 3099, 3065, 1890, 1786 (C=O), 1763 (C=O), 1651, 1611, 1547, 1455, 1345, 1257, 1124, 1097, 961, 892, 830, 774, 702, 529 cm$^{-1}$.

Preparation of S-Phos Ligand 10

2-Dicyclohexylphosphino-2',6'-dimethoxybiphenyl

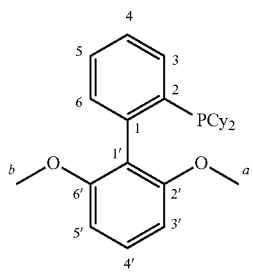

To a solution of 1,3-dimethoxybenzene (2 ml, 15.30 mmol) in anhydrous THF (35 ml) at 0° C., nBuLi (6.2 ml, 15.50 mmol) is added to the dropping funnel for 5 min. The reaction medium is stirred at room temperature for 3.5 h, then 2-bromochlorobenzene (1.6 ml, 13.70 mmol) is added by syringe, dropwise, at 0° C., for 30 min. After 15 min of stirring, the reaction medium is cooled to −78° C. and nBuLi (6.20 ml, 15.50 mmol) is added to the dropping funnel dropwise for 5 min. After 30 min, chlorodicyclohexylphosphine (3.03 ml, 13.70 mmol) is added. The reaction medium is maintained at −78° C. for 1 h, under rapid stirring (mechanical stirring). After returning to room temperature, the precipitate obtained is filtered on a fritted disc containing silica topped with a layer of cellulose acetate, with 600 ml ethyl acetate. The solvents are evaporated with a rotary evaporator, and the orange oil obtained is recrystallized in acetone to obtain S-Phos ligand in the form of white crystals with a yield of 36% (1.22 g, 2.97 mmol).

MP: 163-165° C. (Lit.$^{32}$ MP 162.0-162.5° C.); TLC: (AcOEt/cyclohexane 10/90). $R_f$=0.65; $^1$H-NMR ($CDCl_3$): δ=0.99-1.26 (m, 10H, H(Cy)), 1.60-1.77 (m, 12H, H(Cy)), 3.67 (s, 6H, Me), 6.58 (d, 2H, J=8.2 Hz, $H_{3'}$ and $H_{5'}$), 7.15-7.18 (m, 1H, H(Ar)), 7.18-7.42 (m, 3H, H(Ar)), 7.57 (d, 1H, J=7.4 Hz, H(Ar)) ppm; $^{13}$C-NMR ($CDCl_3$): δ=26.5, 27.3, 27.4, 27.6, 29.0, 29.1, 29.8, 30.1, 33.8, 34.0 (C(Cy)), 55.3 (Cb), 103.1 (Ca), 126.2, 128.2, 128.8 ($C_{3'}$, $C_{4'}$, $C_{5'}$), 130.9, 131.00, 132.4, 135.8 ($C_3$, $C_4$, $C_5$, $C_6$), 135.8, 136.1, 142.7, 143.1, 157.4 ($C_{2'}$, $C_{6'}$) ppm; IR (KBr): υ=3000, 2923, 2851, 1588, 1471, 1442, 1428, 1108 cm$^{-1}$.

General Methods for Suzuki-Miyaura Coupling:

Method A: In a Schlenk tube, under inert atmosphere, containing the brominated derivative (150 mg, 0.59 mmol), boronic acid (1.77 mmol, 3.00 eq), $Na_2CO_3$ (1.77 mmol, 3.00 eq) and Pd(PPh$_3$)$_4$ (0.017 mmol, 3 mol %), toluene (3 ml), $H_2O$ (1.5 ml) and ethanol (0.75 ml) are added. The Schlenk tube is then stoppered with a septum, and the reaction medium carried at 90° C. for 4 h. After returning to room temperature, water (30 ml) is added to the reaction medium. It is extracted with $CH_2Cl_2$ (3×30 ml). The combined organic phases are washed with 30 ml NaCl saturated water solution and dried on $Na_2SO_4$. The solvents are evaporated with a rotary evaporator and the residue is chromatographed on silica.

Method B: In a Schlenk tube, under inert atmosphere, containing the brominated derivative (150 mg, 0.59 mmol), boronic acid (1.77 mmol, 3.00 eq), $K_3PO_4$ (1.77 mmol, 3.00 eq), S-Phos 10 (0.012 mmol, 2 mol %) and Pd(OAc)$_2$ (0.006 mmol, 1 mol %), toluene (3 ml) is added. The Schlenk tube is then stoppered with a septum, and the reaction medium carried at 100° C. for 4 h. After returning to room temperature, $CH_2Cl_2$ (30 ml) is added to the reaction medium. It is filtered on a fritted disc containing silica. The solvents are evaporated with a rotary evaporator and the residue is chromatographed on silica.

Synthesis of Compounds (Z)-4-Phenyl-5-(phenylmethylene)furan-2(5H)-one (4a)

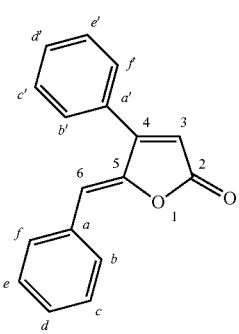

This compound is prepared in accordance with methods A and B, and is purified on silica with a $CH_2Cl_2$/pentane mixture (70/30) as eluent, to give a white solid.

Method A: 74% yield (102 mg, 0.41 mmol); method B: 55% yield (80 mg, 0.32 mmol).

$R_f$=0.58 ($CH_2Cl_2$/pentane, 80:20), MP 124-125° C. $^1$H-NMR ($CDCl_3$): δ=6.18 (s, 1H, 3-H or 6-H), 6.21 (s, 1H, 3-H or 6-H), 7.33 (t, 1H, J=7.3 Hz, a-H), 7.39 (dd, 2H, J=7.8 Hz, J=7.3 Hz, c-H, e-H), 7.54-7.51 (m, 5H, c'-H, d'-H., e'-H, f'-H), 7.81 (d, 2H, J=7.8 Hz, b-H, f-H) ppm. $^{13}$C-NMR ($CDCl_3$): δ=113.9, 114.5 (C-3, C-6), 128.5, 128.8, 129.1, 129.3, 130.4, 130.5, 130.8, 132.9, 147.9 (C-5), 158.8 (C-4), 168.8 (C-2) ppm. IR (KBr): υ=3105, 3056, 1757 (C=O), 1645, 1606, 1585, 1568, 1491, 1449, 1348, 1309, 1218, 1184, 1158, 1088, 1075, 1029, 1000, 954, 914, 867, 840, 815, 757, 690, 658, 638 $cm^{-1}$. UV ($CH_2Cl_2$): $\lambda_{max}$ (ε)=238 (11,100), 339 nm (19,200 l.$mol^{-1}cm^{-1}$). HRMS (EI): calculated for $C_{17}H_{12}O_2$: 248.0837; found 248.0832; $C_{17}H_{12}O_2$ (248.28): C, 82.24, H 4.87; found C 82.06, H 4.96.

(Z)-4-(3-Thiophene)-5-(3-thiophenylmethylene)furan-2(5H)one (4b)

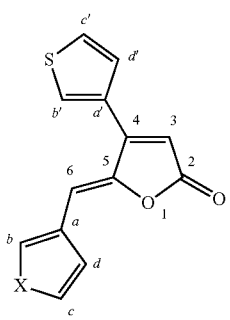

This compound is prepared in accordance with methods A and B, and is purified on silica with a $CH_2Cl_2$/pentane mixture (70/30) as eluent, to give a yellow solid. Method A: 52% yield (53 mg, 0.20 mmol); method B: 72% yield (111 mg, 0.42 mmol).

$R_f$=0.49 ($CH_2Cl_2$/pentane, 70:30), MP 104-106° C. $^1$H-NMR ($CDCl_3$): δ=6.17 (d, 1H, J=0.8 Hz, 6-H), 6.42 (s, 1H, 3-H), 7.29 (dd, 1H, J=5.1 Hz, J=1.3 Hz, c'-H), 7.36 (dd, 1H, J=4.9 Hz, J=2.8 Hz, d-H), 7.52 (dd, 1H, J=5.0 Hz, J=2.9 Hz, d'-H), 7.57 (dd, 1H, J=5.1 Hz, J=1.3 Hz, c-H), 7.64 (dd, 1H, J=2.9 Hz, J=1.4 Hz, b-H), 7.79-7.80 (m, 1H, b'-H) ppm. $^{13}$C-NMR ($CDCl_3$): δ=107.4 (C-6), 113.2 (C-3), 126.2, 126.5, 127.4, 127.5, 128.8, 129.0, 130.9, 134.4, 146.9 (C-5), 152.4 (C-4), 168.8 (C-2) ppm. IR (KBr): υ=3100, 3073, 1749 (C=O), 1740 (C=O), 1647, 1591, 1501, 1409, 1333, 1300, 1234, 1093, 979, 955, 934, 881, 867, 860, 831, 801, 785, 763, 688, 674, 628, 609, 602 $cm^{-1}$. UV ($CH_2Cl_2$): $\lambda_{max}$ (ε)=229 (13,100), 287 nm (12,300 l.$mol^{-1}cm^{-1}$). HRMS (EI): calculated for $C_{13}H_8O_2S_2$: 259.9966. found 259.9969; $C_{13}H_8O_2S_2$ (260.33): C 59.98; H 3.10; found C 59.90; H 3.13.

(Z)-4-(2-naphthalene)-5-(2-naphthalenephenylmethylene)furan-2(5H)-one (4c)

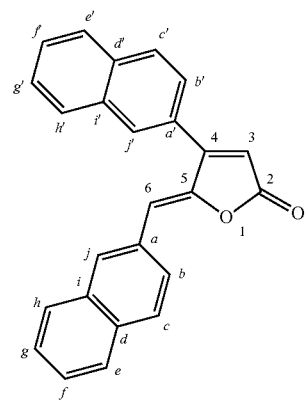 [SMILES: O=C1C=C(c2ccc3ccccc3c2)/C(=C/c2ccc3ccccc3c2)O1]

This compound is prepared in accordance with methods A and B, and is purified on silica with a $CH_2Cl_2$/pentane mixture (70/30) as eluent, to give a yellow solid. Method A: 63% yield (129 mg, 0.37 mmol); method B: the product obtained is recrystallized in an AcOEt/cyclohexane mixture: 35% yield (72 mg, 0.21 mmol).

$R_f$=0.46 ($CH_2Cl_2$/pentane, 70:30), MP 173-174° C. $^1$H NMR ($CDCl_3$): δ=6.32 (s, 1H, 3-H or 6-H), 6.42 (s, 1H, 3-H or 6-H). 7.46-7.53 (m, 2H, ArH), 7.58-7.65 (m, 3H, ArH), 7.80-7.87 (m, 3H, ArH), 7.93-8.03 (m, 5H, ArH), 8.21 (s, 1H, ArH) ppm. $^{13}$C-NMR ($CDCl_3$): δ=114.3, 114.6 (C-3, C-6), 125.5, 126.5, 127.2, 127.2, 127.4, 127.7, 127.9, 128.5, 128.5, 128.6, 128.7, 129.0, 130.6, 131.2, 132.9, 133.3, 133.4, 133.9, 148.3 (C-5), 158.9 (C-4), 169.0 (C-2) ppm. IR (KBr): υ=3094, 3048, 1775 (C=O), 1643, 1628, 1607, 1581, 1565, 1506, 1371, 1343, 1315, 1272, 1187, 1130, 1082, 977, 942, 920, 898, 886, 856, 848, 821, 814, 790, 769, 740 $cm^{-1}$. UV ($CH_2Cl_2$): $\lambda_{max}$ (ε)=279 (21,000), 352 nm (22,000 l.$mol^{-1}cm^{-1}$). HRMS (EI): calculated for $C_{25}H_{16}O_2$: 348.1150; found 348.1136; $C_{25}H_{16}O_2$ (348.39): C 86.19, H 4.63; found C 85.98; H 4.80.

(Z)-5-(3,4-Dimethoxyphenylmethylene)-4-(3,4-dimethoxyphenyl-methylene)furan-2(5H)-one (4d)

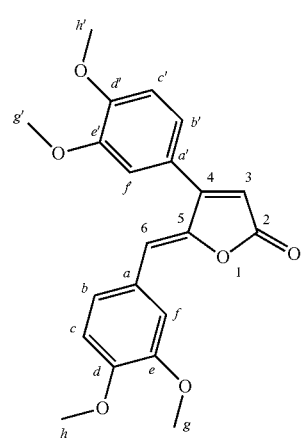 [SMILES: COc1ccc(/C=C2\OC(=O)C=C2c2ccc(OC)c(OC)c2)cc1OC]

Method A: Synthesis is carried out from 1 g of (Z)-4-bromo-5-(bromomethylene)furan-2(5H)-one 2. The product obtained is purified on silica with a CH₂Cl₂/AcOEt mixture (93/7) as eluent, then recrystallized in a AcOEt/cyclohexane mixture to give green crystals with a yield of 47% (691 mg, 1.87 mmol).

$R_f$=0.66 (CH₂Cl₂/EtOAc, 93:7), MP 165-167° C. ¹H-NMR (CDCl₃): δ=6.12 (s, 1H, 3-H), 6.18 (s, 1H, 6-H), 6.88 (d, 1H, J=8.5 Hz, e-H), 6.99 (d, 1H, J=1.8 Hz, b'-H), 7.01 (d, 1H, J=8.2 Hz, e'-H), 7.12 (dd, 1H, J=8.2 Hz, J=2.1 Hz, f'-H), 7.32 (dd, 1H, J=8.5 Hz, J=2.1 Hz, f-H), 7.48 (d, 1H, J=2.1 Hz, b-H) ppm. ¹³C-NMR (CDCl₃): δ=55.9, 56.0, 56.1, 56.2, 111.0, 111.3, 111.5, 112.4, 112.6 (C-3), 112.9, 113.9, 114.0 (C-6), 121.6, 123.1, 124.9, 126.2, 146.1, 146.8 (C-5), 149.3, 150.3, 150.9, 158.5 (C-4), 169.2 (C-2) ppm. IR (KBr): υ=2935, 2837, 1749 (C=O), 1646, 1581, 1510, 1424, 1329, 1243, 1167, 1144, 1025, 930, 876, 811, 765, 750, 597 cm⁻¹. UV (CH₂Cl₂): $\lambda_{max}$ (ε)=263 (16,400), 373 nm (20,700 l.mol⁻¹ cm⁻¹). HRMS (EI): calculated for C₂₁H₂₀O₆: 368.1259; found 368.1248; C₂₁H₂₀O₆ (368.38): C 68.47, H 5.47; found C 67.31, H 5.49.

(Z)-4-(tert-Butyl-hydroxyphenylcarbamate)-(Z)-5 (tert-butylmethylene-hydroxyphenyl-carbamate) furan-2(5H)-one (4e)

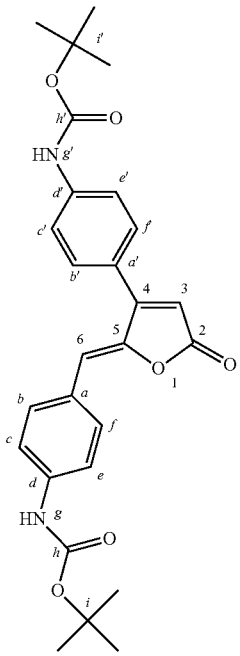 [SMILES: CC(C)(C)OC(=O)Nc1ccc(/C=C2\OC(=O)C=C2c2ccc(NC(=O)OC(C)(C)C)cc2)cc1]

This compound is prepared in accordance with methods A and B, and is purified on silica with an Et₂O/pentane mixture (40/60) as eluent, to give a yellow solid. Method A: 52% yield (148 mg, 0.31 mmol); method B: the product obtained is recrystallized in CH₂Cl₂: 25% yield (47 mg, 0.10 mmol).

$R_f$=0.68 (Et₂O/pentane, 60:40), MP 140-142° C. dec. ¹H-NMR (CDCl₃): δ=1.53 (s, 9H, CH₃), 1.55 (s, 9H, CH₃), 6.13 (s, 1H, 3-H or 6-H), 6.14 (s, 1H, 3-H or 6-H), 6.62 (s, 1H, h-H or h'-H), 7.41 (d, 2H, J=8.9 Hz, b-H, f-H or b'-H, f'-H), 7.45 (d, 2H, J=8.9 Hz, b-H, f-H or b'-H, f'-H), 7.53 (d, 2H, J=8.6 Hz, c-H, e-H or c'-H, e'-H), 7.75 (d, 2H, J=8.6 Hz, b-H, f-H or b'-H, f'-H) ppm. ¹³C-NMR (CDCl₃): δ=28.3 (CH₃), 81.0, 81.4, 112.8 (C-6 or C-3), 113.6 (C-6 or C-3), 118.2, 118.6, 124.9, 127.8, 129.4, 131.9, 139.4, 140.6 147.1 (C-5), 152.4, 152.5, 158.3 (C-4), 169.2 (C-2) ppm. IR (KBr): υ=3298, 2982, 1737 (C=O), 1694 (C=O), 1592, 1522, 1413, 1319, 1238, 1158, 1054, 956, 930, 838, 522 cm⁻¹. UV (CH₂Cl₂): $\lambda_{max}$ (ε)=249 (25,000), 351 nm (20,600 l.mol⁻¹ cm⁻¹). HRMS (EI): calculated for C₂₇H₃₀N₂O₆: 378.1580; found 378.1587 (M-CO₂—C₄H₈⁺); C₂₇H₃₀N₂O₆ (478.54): C 67.77, H 6.32, N 5.85; found C 67.50, H 6.57, N 5.61.

(Z)-4-(2-Fluorophenyl)-(Z)-5-(2-fluorophenylmethylene)furan-2(5H)-one (4f)

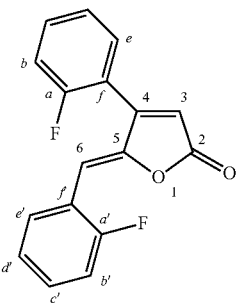 [SMILES: O=C1C=C(c2ccccc2F)/C(=C/c2ccccc2F)O1]

Method B: The product obtained is purified on silica with a CH₂Cl₂/pentane mixture (50/50) as eluent, to give a white solid with 71% yield (119 mg, 0.42 mmol).

$R_f$=0.48 (CH₂Cl₂/pentane, 50:50), MP 151-153° C. ¹H-NMR (CDCl₃): δ=6.20 (s, 1H, 3-H), 6.83 (s, 1H, 6-H), 7.29-7.46 (m, 5H, ArH), 7.63-7.65 (m, 2H, ArH), 8.08-8.14 (m, 1H, H ArH) ppm. ¹³C-NMR (CDCl₃): δ=104.5 (d, $J^3_{F-C}$=8 Hz, C-6), 115.3 (d, $J^2_{F-C}$=22 Hz, C-b or C-b'), 116.7 (d, $J^2_{F-C}$=22 Hz, C-b or C-b'), 117.6 (d, $J^3_{F-C}$=3 Hz, C-c or C-c' or C-e or C-e'), 117.9 (d, $J^2_{F-C}$=15 Hz, C-f or C-f'), 124.6 (C-3), 124.7 (d, $J^3_{F-C}$=3 Hz, C-c or C-c' or C-e or C-e'), 130.5 (d, $J^4_{F-C}$=2 Hz, C-d or C-d'), 131.00 (d, $J^3_{F-C}$=9 Hz, C-c or C-c' or C-e or C-e'), 131.6 (d, $J^4_{F-C}$=1 Hz, C-d or C-d'), 132.3 (d, $J^3_{F-C}$=8 Hz, C-c or C-c' or C-e or C-e'), 150.3, 152.1 (C-4, C-5), 158.34 (d, $J^1_{F-C}$=78 Hz, C-a or C-a'), 162.1 (d, $J^1_{F-C}$=80 Hz, C-a or C-a'), 168.5 (C-2) ppm. IR (KBr): υ=3104, 1777 (C=O), 1621, 1573, 1481, 1455, 1343, 1235, 1208, 1116, 1079, 964, 927, 873, 848, 825, 805, 793, 760, 750, 679, 462 cm⁻¹. UV (CH₂Cl₂): $\lambda_{max}$ (ε)=238 (15,000), 341 nm (30,300 l.mol⁻¹cm⁻¹). HRMS (EI): calculated for C₁₇H₁₀F₂O₂: 284.0649; found 284.0628; C₁₇H₁₀F₂O₂ (284.06): C 71.83, H 3.55; found C 71.60, H 3.62.

5-(Diphenylmethylene)furan-2(5H)-one (5a)

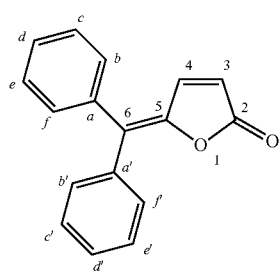

The crude reaction product obtained is purified on silica gel with a CH$_2$Cl$_2$/pentane mixture (70/30) as eluent, to give a white solid. Method A: 62% yield (90 mg, 0.36 mmol); method B: 83% yield (162 mg, 0.65 mmol).

$R_f$=0.51 (CH$_2$Cl$_2$/pentane, 70:30), MP 110-112° C. $^1$H-NMR (CDCl$_3$): δ=6.21 (d, 1H, J=5.4 Hz, 3-H), 7.26-7.52 (m, 11H, 4-H, b-H, c-H, d-H, e-H, f-H, b'-H, c'-H, d'-H, e'-H, f'-H) ppm. $^{13}$C-NMR (CDCl$_3$): δ=118.6 (C-3), 128.2, 128.5, 128.9, 129.1, 131.2, 136.5, 137.9 (C-6), 143.9 (C-4), 147.12 (C-5), 170.5 (C-2) ppm. IR (KBr): υ=3096, 1767 (C=O), 1745 (C=O), 1546, 1490, 1443, 1230, 1114, 1085, 957, 932, 877, 823, 774, 719, 697 cm$^{-1}$. UV (CH$_2$Cl$_2$): λ$_{max}$ (ε)=245 (13,500), 344 nm (22,200 l.mol$^{-1}$cm$^{-1}$). HRMS (EI): calculated for C$_{17}$H$_{12}$O$_2$: 248.0837; found 248.0835; C$_{17}$H$_{12}$O$_2$ (248.28): C 82.24, H 4.87; found: C 82.08, H, 4.92.

5-(Dithiophene-3-ylmethylene)furan-2-(5H)-one (5b)

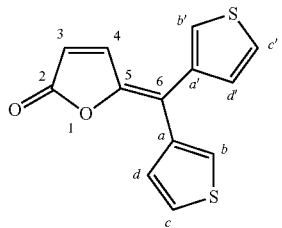 [SMILES: O=C1C=CC(=C(c2ccsc2)c2ccsc2)O1]

This compound is prepared in accordance with methods A and B, and is purified on silica with a CH$_2$Cl$_2$/pentane mixture (70/30) as eluent, to give a light yellow solid. Method A: 66% yield (338 mg, 1.3 mmol); method B: is prepared from 500 mg 5-(dibromomethylene)furan-2-(5H)one 3, after the column the product is recrystallized in a CH$_2$Cl$_2$/Et$_2$O) mixture: 40% yield (205 mg, 0.78 mmol).

$R_f$=0.50 (CH$_2$Cl$_2$/pentane, 70:30), MP 122-124° C. $^1$H-NMR (CDCl$_3$): δ=6.16 (d, 1H, J=5.4 Hz, 3-H), 7.10 (dd, 1H, J=4.9 Hz, J=1.3 Hz), 7.32-7.35 (m, 2H.), 7.43 (dd, 1H, J=4.9 Hz, J=3.1 Hz), 7.46 (d, 1H, J=5.4 Hz, 4-H), 7.52 (dd, 1H, J=5.1 Hz, J=1.3 Hz), 7.55 (dd, 1H J=2.8 Hz, J=1.3 Hz) ppm. $^{13}$C-NMR (CDCl$_3$): δ=117.8 (C-3), 118.0 (C-6), 125.5, 126.2, 126.7, 129.4, 129.6, 129.8, 136.7, 137.3, 143.6 (C-4), 146.4 (C-5), 170.2 (C-2) ppm. IR (KBr): υ=3109, 1761 (C=O), 1740 (C=O), 1608, 1540, 1507, 1420, 1293, 1234, 1197, 1158, 1113, 1069, 994, 978, 909, 894, 841, 745, 705, 685, 620, 521 cm$^{-1}$. UV (CH$_2$Cl$_2$): λ$_{max}$ (ε)=229 (15,300), 359 nm (24,900 l.mol$^{-1}$cm$^{-1}$). HRMS (EI): calculated for C$_{13}$H$_8$O$_2$S$_2$: 259.9966; found 259.9969; C$_{13}$H$_8$O$_2$S$_2$ (260.33): C 59.98, H 3.10; found C 59.89, H 3.05.

5-(Dinaphthalene-2-ylmethylene)furan-2-(5H)-one (5c)

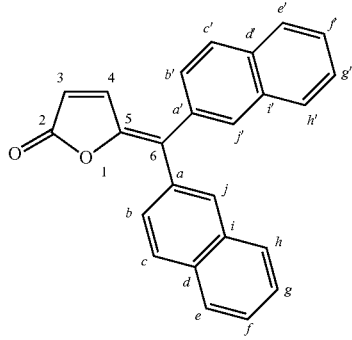 [SMILES: O=C1C=CC(=C(c2ccc3ccccc3c2)c2ccc3ccccc3c2)O1]

This compound is prepared in accordance with methods A and B, and is purified on silica with a CH$_2$Cl$_2$/pentane mixture (30/70) as eluent, to give a yellow solid. Method A: 57% yield (56 mg, 0.33 mmol); method B: 88% yield (182 mg, 0.52 mmol);

$R_f$=0.63 (CH$_2$Cl$_2$/pentane, 70:30), MP 138-140° C. $^1$H-NMR (CDCl$_3$): δ=6.25 (d, 1H, J=5.6 Hz, 3-H), 7.33-7.93 (m, 15H) ppm. $^{13}$C-NMR (CDCl$_3$): δ=118.6 (C-3, C-6), 126.4, 126.9, 127.1, 127.2, 127.6, 127.8, 128.1, 128.2, 128.3, 128.5, 128.9, 130.8, 131.7, 132.9, 132.9, 133.3, 133.3, 134.0, 134.7, 144.0 (C-4), 147.7, (C-5), 170.5 (C-2) ppm. IR (KBr): υ=3054, 1777 (C=O), 1752 (C=O), 1597, 1544, 1503, 1357, 1244, 1190, 1109, 938, 888, 821, 749, 709, 476 cm$^{-1}$. UV (CH$_2$Cl$_2$): λ$_{max}$ (ε)=230 (48,600), 238 (49,800), 256 (45,900), 363 nm (27,600 l.mol$^{-1}$cm$^{-1}$). HRMS (EI): calculated for C$_{25}$H$_{16}$O$_2$: 348.1150; found 348.1140. C$_{25}$H$_{16}$O$_2$ (348.39): C 86.19, H 4.63; found C 86.03, H 4.75.

5-(bis(3,4-Dimethoxyphenyl)methylene)furan-2-(5H)-one (5d)

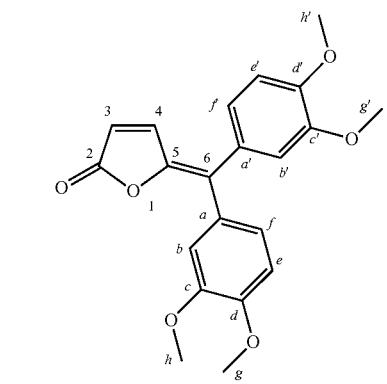 [SMILES: COc1ccc(C(=C2C=CC(=O)O2)c2ccc(OC)c(OC)c2)cc1OC]

—Via Suzuki-Miyaura Coupling

The compound (5d) is prepared in accordance with methods A and B, and is purified on silica with a CH$_2$Cl$_2$/Et$_2$O mixture (92/8) as eluent, to give a yellow oil. Method A: 50% yield (107 mg, 0.29 mmol); method B: 25% yield (51 mg, 0.14 mmol).

$R_f$=0.52 (CH$_2$Cl$_2$/Et$_2$O, 92:8), Rf (EtOAc/cyclohexane 1:2)=0.21

MP 160-162° C. $^1$H-NMR (CDCl$_3$): δ=3.83 (s, 3H, g-H, h-H, g'-H, or h'-H), 3.84 (s, 3H, g-H, h-H, g'-H, or h'-H), 3.92 (s, 3H, g-H, h-H, g'-H, or h'-H), 3.96 (s, 3H, g-H, H, h-H, g'-H, or h'-H), 6.15 (d, 1H, J=5.4 Hz, 3-H), 6.76 (d, 1H, J=1.8 Hz, b'-H), 6.85 (d, 1H, J=8.5 Hz, e-H), 6.86-6.95 (m, 2H, f'-H, e'-H), 7.07 (dd, 1H, J=8.5 Hz, J=2.0 Hz, f-H), 7.17 (d, 1H, J=2.0 Hz, b-H), 7.41 (d, 1H, J=5.4 Hz, 4-H) ppm. $^{13}$C-NMR (CDCl$_3$): δ=55.9, 56.0, 56.0, 110.7, 110.7, 114.2, 114.3, 117.3 (C-3), 124.3, 125.3, 128.6 (C-6), 129.3, 129.8, 114.0 (C-4), 146.3 (C-5), 148.5, 148.8, 149.8, 150.1, 170.7 (C-2) ppm. IR (KBr): υ=3132, 3107, 3059, 2999, 2957, 2934, 2910, 2836, 1778 (C=O), 1747 (C=O), 1595, 1577, 1538, 1511, 1462, 1413, 1349, 1321, 1306, 1252, 1239, 1211, 1171, 1140, 1111, 1069, 1023, 999, 981, 895, 862, 810, 761, 734, 710, 688 cm$^{-1}$. UV (CH$_2$Cl$_2$): λ$_{max}$ (ε)=263 (17,700), 384 nm (19,900 l.mol$^{-1}$cm$^{-1}$). HRMS (EI): calculated for C$_{21}$H$_{20}$O$_6$: 368.1260; found 368.1248; C$_{21}$H$_{20}$O$_6$ (368.38): C 68.47, H 5.47; found C 68.28, H 5.64.

—Via Coupling of 2-methoxyfurane with a Ketone:

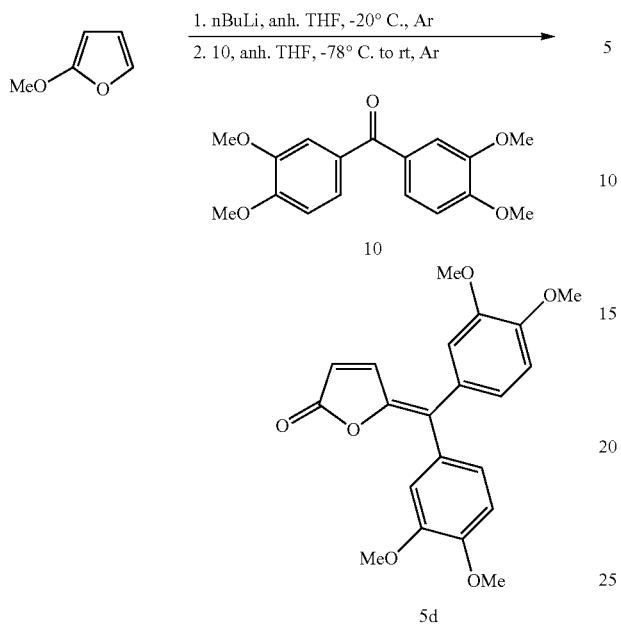

n-BuLi (2.5 M in hexane, 3.44 ml, 8.64 mmol) is added to a solution of 2-methoxyfurane (0.80 ml, 8.64 mmol, 1.3 eq) in 30 ml anhydrous THF at −20° C. and under argon. The pale yellow solution is stirred for 1.5 h at −20° C. The orange solution obtained is then cooled to −78° C. and a solution of ketone 10 (2.00 g, 6.61 mmol, 1.0 eq., Eur. J. Org. Chem., 2004, 2381) in 40 ml anhydrous THF is added dropwise. The bath is then withdrawn and the mixture is stirred at room temperature overnight.

The reaction is quenched by adding a 1 N HCl solution and is left stirring for one hour. The product is then extracted with ethyl acetate.

The solvent is evaporated to lead to a solid. After washing with ether, the product is obtained in the form of a yellow solid with a yield of 83% (2.04 g).

5-(bis(4-tert-Butyl-hydroxyphenylcarbamate)furan-2-(5H)-one 5e)

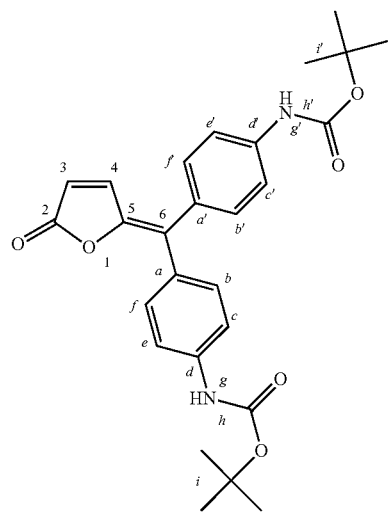 [SMILES: CC(C)(C)OC(=O)Nc1ccc(C(=C2C=CC(=O)O2)c2ccc(NC(=O)OC(C)(C)C)cc2)cc1]

Method B: The compound is prepared from 200 mg 5-(dibromomethylene)furan-2-(5H)one 3. The product obtained is purified on silica with a $CH_2Cl_2$/AcOEt mixture (90/10) as eluent, to give a yellow solid with 86% yield (319 mg, 0.67 mmol).

$R_f$=0.51 ($CH_2Cl_2$/EtOAc, 95:5), MP 138-140° C. $^1$H-NMR (CDCl$_3$): δ=1.52 (s, 9H, O—CH$_3$), 1.54 (s, 9H, O—CH$_3$), 6.16 (d, 1H, J=5.4 Hz, 3-H), 6.67 (s, 1H, N-H), 6.70 (s, 1H, N-H), 7.16 (s, 1H), 7.19 (s, 1H), 7.34-7.46 (m, 7H), 7.40 (d, 1H, J=5.4 Hz, 4-H) ppm. $^{13}$C-NMR (CDCl$_3$): δ=28.3 (CH$_3$), 80.9, 81.0, 117.5 (C-3), 117.8, 118.2, 128.3 (C-6), 131.1, 131.6, 132.1, 132.4, 139.2, 139.25, 143.8 (C-4), 146.5 (C-5), 152.4, 152.6, 170.8 (C-2) ppm. IR (KBr): υ=3322 (N-H), 2977, 1773 (C=O), 1735 (C=O), 1708 (C=O), 1586, 1521, 1408, 1392, 1367, 1315, 1232, 1157, 1052, 1016, 961, 923, 882, 842, 809, 771, 708 cm$^{-1}$. UV (CH$_2$Cl$_2$): λ$_{max}$ (ε)=259 (22,600), 377 nm (24,900 l.mol$^{-1}$cm$^{-1}$). C$_{27}$H$_{30}$N$_2$O$_6$ (478.54): C 67.77, H, 6.32, N 5.85; found C 67.61, H 6.41, N 5.84.

5-bis((2-fluorophenyl)methylene)furan-2-(5H)-one (5f)

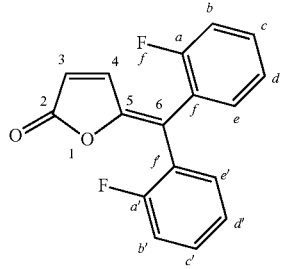 [SMILES: O=C1C=CC(=C(c2ccccc2F)c2ccccc2F)O1]

Method B: The product obtained is purified on silica with a $CH_2Cl_2$/pentane mixture (70/30) as eluent, to give a white solid with 80% yield (122 mg, 0.43 mmol).

$R_f$=0.45 (CH$_2$Cl$_2$/pentane, 70:30), MP 138-139° C. $^1$H-NMR (CDCl$_3$): δ=6.29 (d, 1H, J=5.6 Hz, 3-H), 7.05-7.44 (m, 9H) ppm. $^{13}$C-NMR (CDCl$_3$): δ=116.0 (d, J$^2_{F-C}$=46 Hz, C-b or C-b'), 116.3 (d, J$^2_{F-C}$=46 Hz, C-b or C-b'), 120.7 (C-3), 124.1 (dd, J$^2_{F-C}$=82 Hz, J$^4_{F-C}$=14 Hz, C-f or C-f'), 130.8 (d, J$^3_{F-C}$=29 Hz, C-c, C-e, C-c', C-e'), 130.9 (d, J$^3_{F-C}$=27 Hz, C-c, C-e, C-c', C-e'), 131.7 (d .J$^4_{F-C}$=11 Hz, C-d or C-d'), 132.5 (d, J$^4_{F-C}$=8 Hz, C-d or C-d'), 142.4 (C-6), 142.4 (C-4), 149.0 (C-5), 158.3 (d, J$^1_{F-C}$=91 Hz, C-a or C-a'), 162.0 (d, J$^1_{F-C}$=80 Hz, C-a or C-a'), 169.5 (C-2) ppm. IR (KBr) υ=3146, 3123, 3078, 3039, 1779 (C=O), 1752 (C=O), 1641, 1608, 1577, 1552, 1485, 1444, 1258, 1244, 1225, 1183, 1117, 1074, 1033, 971, 958, 886, 813, 771, 742, 647, 621, 538 cm$^{-1}$. UV (CH$_2$Cl$_2$): λ$_{max}$ (ε)=244 (15,300), 328 nm (19,300 l.mol$^{-1}$cm$^{-1}$). HRMS (EI): calculated for C$_{17}$H$_{10}$O$_2$F$_2$: 284.0649; found 284.0628; C$_{17}$H$_{10}$O$_2$F$_2$ (284.26): C 71.83, H 3.55; found C, 71.66, H 3.67.

5-(bis(3,4,5-trimethoxyphenyl)methylene)furan-2-(5H)-one (5h)

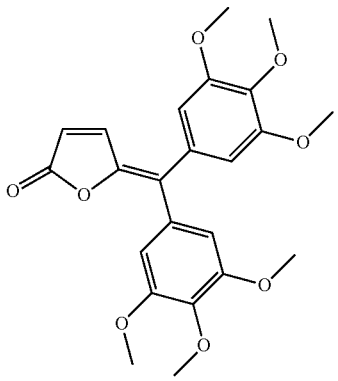 [SMILES: COc1cc(C(=C2C=CC(=O)O2)c2cc(OC)c(OC)c(OC)c2)cc(OC)c1OC]

Compound 5h is prepared in accordance with method A and is purified on silica with a cyclohexane/ethyl acetate mixture (1/1) as eluent, to give a yellow solid with a yield of 70%.

Rf (EtOAc/cyclohexane 1:1)=0.51
HRMS calc. for M$^+$ 428.1471, found 428.1471.
$\delta_H$ (270 MHz, CDCl$_3$): 7.46 (1H, d, J=5.38 Hz, 0.1H olefinic), 6.78 (2H, s, 2H aromatic), 6.51 (2H, s, 2H aromatic), 6.20 (1H, d, J=5.38 Hz, 1H olefinic), 3.93 (3H, s, OMe), 3.90 (3H, s, OMe), 3.84 (6H, s, 2×OMe), 3.81 (6H, s, 2×OMe).
$\delta_C$ (67.80 MHz, CDCl$_3$): 170.24, 153.03, 152.76, 146.78, 143.95, 132.32, 131.50, 128.35, 118.04, 109.07, 108.78, 56.31.

5-(bis(3,4-dihydroxyphenyl)methylene)furan-2-(5H)-one (5 g)

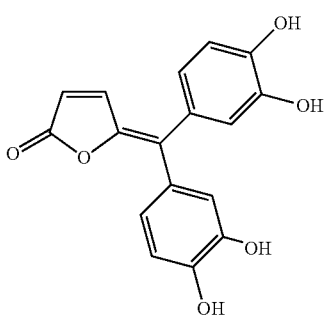 [SMILES: O=C1C=CC(=C(c2ccc(O)c(O)c2)c2ccc(O)c(O)c2)O1]

To a solution of compound 5d (400 mg, 1.08 mmol) in 15 ml anhydrous dichloromethane under argon, 0° C. BBr$_3$ (1 M in DCM, 10.86 ml, 10.86 mmol, 10 eq) is added. The red solution is then stirred for 1 hour at 0° C., the reaction is then quenched by adding 1 N HCl solution and then the aqueous phase is extracted with ethyl acetate. The organic phase is washed with water, then with saturated NaCl solution and finally dried on MgSO$_4$. The solvent is evaporated and the solid obtained is washed with ether and dried under a vacuum to lead to a pale green solid with a yield of 73% (249 mg).

Rf (EtOAc/MeOH 95:5)=0.75
HRMS calc. for M$^+$366.1943
$\delta_H$ (270 MHz, acetone): 8.39 (1H, bs, 1×OH), 8.37 (1H, bs, 1×OH), 8.29 (1H, bs, 1×OH), 8.26 (1H, bs, 1×OH), 7.56 (1H, d, J=5.44 Hz, H furan), 7.09 (1H, d, J=1.86 Hz, H aromatic), 6.92 (1H, d, J=8.05 Hz, H aromatic), 6.87-6.86 (2H, m, H aromatic), 6.76 (1H, d, J=2.01 Hz, H aromatic), 6.67 (1H, dd, J=2.08 and 8.05 Hz, H aromatic), 6.21 (1H, d, J=5.41 Hz, H furan).
$\delta_C$ (67.80 MHz, acetone): 172.14, 148.37, 147.99, 147.67, 146.76, 146.35, 146.29, 130.99, 130.85, 130.46, 126.00, 125.22, 120.15, 120.12, 118.29, 116.89, 116.75.

5-(bis(3,4,5-Trihydroxyphenyl)methylene)furan-2-(5H)-one (5i)

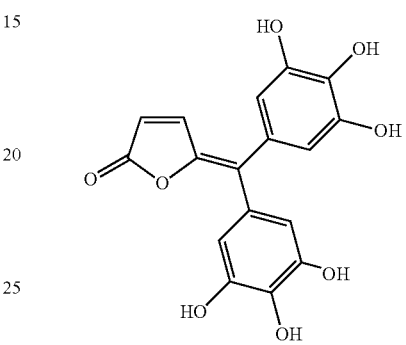

Compound 5i is prepared in accordance with the method used for the synthesis of compound 5g starting with 200 mg of 5h with a yield of 93% (159 mg, blue-green solid).

Rf (EtOAc/MeOH 90:10)=0.70;
HRMS calc. for M$^+$ 344.0532,
$\delta_H$ (270 MHz, acetone): 8.12 (3H. d 0.3×OH), 7.73 (1H, d, 1×OH), 7.56 (1H, d, J=5.38 Hz, 1H olefinic), 6.64 (2H, s, 2H aromatic), 6.33 (2H, s, 2H aromatic), 6.17 (1H, d, J=5.63 Hz, 1H olefinic), 2.19 (1H, bs, 1×OH);
$\delta_C$ (67.80 MHz, acetone): 171.16, 146.65, 146.18, 145.82, 145.46, 135.35, 134.57, 129.62, 129.17, 128.71, 117.04, 111.83, 111.55.

(Z)-4-Bromo-5-(phenylmethylene)furan-2-(5H)-one (6a)

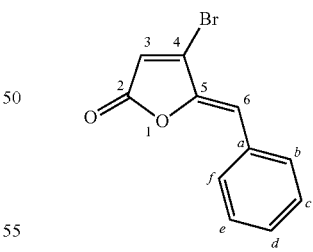

In a Schlenk tube, under inert atmosphere, containing 2 (200 mg, 0.78 mmol), phenylboronic acid (122 mg, 1.18 mmol), Na$_2$CO$_3$ (167 mg, 1.57 mmol) and Pd(PPh$_3$)$_4$ (27 mg, 3 mol %), toluene (4 ml), H$_2$O (2 ml) and ethanol (1 ml) are added. The Schlenk tube is then stoppered with a septum, and the reaction medium is stirred for 2 days at room temperature. Water (10 ml) is then added, and the reaction medium is extracted with ether (3×30 ml). The combined organic phases are washed with NaCl saturated water solution and dried on Na$_2$SO$_4$. The solvents are evaporated with a rotary evaporator, and the residue is chromatographed on silica, with an Et2O/pentane mixture (5/95) as eluent. An orange yellow solid is obtained with a yield of 47% (94 mg, 0.37 mmol).

$R_f$=0.84 (CH$_2$Cl$_2$/pentane, 50:50), MP 68-70° C. $^1$H-NMR (CDCl$_3$): δ=6.37 (s, 1H, 6-H), 6.42 (s, 1H, 3-H), 7.37-7.46 (m, 3H, c-H, d-H, e-H), 7.80 (d, 1H, J=1.3 Hz, b-H or f-H), 7.83 (d, 1H, J=1.6 Hz, b-H or f-H) ppm. $^{13}$C-NMR (CDCl$_3$): δ=113.5 (C-6), 118.8 (C-3), 129.0, 129.9, 131.0, 138.5, 138.5 (C-5), 146.6 (C-4), 167.1 (C-2) ppm. IR (KBr): υ=3503, 3137, 3051, 3023, 2925, 1761 (C=O), 1645 (C=C), 1595, 1550, 1525, 1490, 1447, 1352, 1322, 1300, 1285, 1214, 1179, 1105, 1075, 1032, 999, 968, 911, 866, 848, 815, 753, 687, 668, 626, 613, 528 cm$^{-1}$. UV (CH$_2$Cl$_2$): $\lambda_{max}$ (ε)=341 nm (29,800 l.mol$^{-1}$cm$^{-1}$). C$_{11}$H$_7$O$_2$Br (251.08): C 52.62, H 2.81; found C 52.82, H 3.02.

(Z)-5-(Phenylmethylene)-4-(thiophene-3-yl)furan-2-(5H)-one (8a)

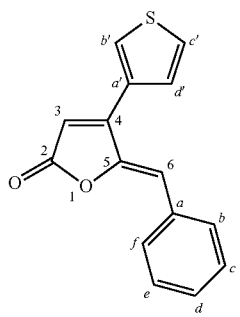

In a Schlenk tube, under inert atmosphere, containing 6a (94 mg, 0.37 mmol), thiophene-3-boronic acid (0.71 mg, 0.56 mmol), Na$_2$CO$_3$ (79 mg, 0.75 mmol) and Pd(PPh$_3$)$_4$ (13 mg, 3 mol %), toluene (3 ml), H$_2$O (1.5 ml) and ethanol (0.75 ml) are added. The Schlenk tube is then stoppered with a septum, and the reaction medium carried at 90° C. for 6 h. After returning to room temperature, water (30 ml) is added to the reaction medium. It is extracted with CH$_2$Cl$_2$ (3×20 ml). The combined organic phases are washed with 20 ml NaCl saturated water solution and dried on Na$_2$SO$_4$. The solvents are evaporated with a rotary evaporator, and the residue is chromatographed on silica with an Et$_2$O/pentane mixture (10/90) as eluent. A pale pink solid is obtained with 48% yield (45 mg, 0.18 mmol).

$R_f$=0.55 (Et$_2$O/pentane, 20:80), MP 87-89° C. $^1$H-NMR (CDCl$_3$): δ=6.21 (s, 1H, 3-H), 6.34 (s, 1H, 6-H), 7.31 (dd, 1H, J=4.9 Hz, J=1.3 Hz, c'-H), 7.39 (m, 3H, c-H, d-H, e-H), 7.53 (dd, 1H, J=5.0 Hz, J=2.9 Hz, d'-H). 7.65 (dd, 1H, J=2.9 Hz, J=1.4 Hz, b'-H), 7.82 (d, 1H, J=1.0 Hz, b-H or f-H), 7.84 (1H, J=1.8 Hz, b-H or f-H) ppm. $^{13}$C-NMR (CDCl$_3$): δ=113.4 (C-6, C-3), 126.6, 127.5, 128.8, 129.3, 130.8, 130.9, 132.9, 147.8 (C-5), 152.9 (C-4), 169.0 (C-2) ppm. IR (KBr): υ=3100, 3063, 1753 (C=O), 1712, 1681, 1591, 1503, 1493, 1447, 1421, 1305, 1223, 1184, 1093, 978, 939, 922, 871, 830, 802, 767, 756, 690, 678, 650, 610, 552, 534 cm$^{-1}$. UV (CH$_2$Cl$_2$): $\lambda_{max}$ (ε)=236 (14,700), 339 nm (24,200 l.mol$^-$ $^1$cm$^{-1}$). HRMS (EI): calculated for C$_{15}$H$_{10}$O$_2$S: 254.0401; found: 254.0398; C$_{15}$H$_{10}$O$_2$S (254.31): C 70.84, H 3.96; found C 70.73, H 4.05.

(Z)-4-Bromo-5-(thiophene-3-ylmethylene)furan-2-(5H)-one (6b)

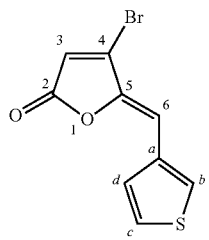 [SMILES: O=C1C=C(Br)/C(=C/c2ccsc2)O1]

In a Schlenk tube, under inert atmosphere, containing 2 (200 mg, 0.78 mmol), thiophene-3-boronic acid (110 mg, 0.86 mmol), K$_3$PO$_4$ (334 mg, 1.57 mmol), S-Phos 10 (6 mg, 2 mol %) and Pd(OAc)$_2$ (27 mg, 3 mol %), toluene (3 ml) is added. The Schlenk tube is then stoppered with a septum, and the reaction medium is stirred for 5 h at room temperature. CH$_2$Cl$_2$ (30 ml) is added to the reaction medium which is then filtered on a fritted disc containing a small amount of silica. The solvents are evaporated with a rotary evaporator, and the residue is chromatographed on silica, with a CH$_2$Cl$_2$/pentane mixture (50/50) as eluent. A yellow solid is obtained with 27% yield (54 mg, 0.21 mmol).

$R_f$=0.78 (CH$_2$Cl$_2$/pentane 50:50), MP 68-70° C. $^1$H-NMR (CDCl$_3$): δ=6.38 (s, 1H, 6-H), 6.45 (s, 1H, 3-H), 7.37 (dd, 1H, J=5.1 Hz, J=2.8 Hz, d-H), 7.56 (d, 1H, J=5.1 Hz, c-H), 7.82 (d, 1H, J=1.8 Hz, b-H) ppm. $^{13}$C-NMR (CDCl$_3$): δ=107.6 (C-6), 118.6 (C-3), 126.5, 128.7, 129.8, 133.6, 137.9 (C-5), 145.8 (C-4), 167.0 (C-2) ppm. IR (KBr) υ=3122, 3062, 2924, 1752 (C=O), 1650, 1545, 1508, 1414, 1385, 1333, 1288, 1243, 1222, 1192, 1173, 1148, 1110, 1080, 976, 951, 939, 910, 881, 852, 835, 821, 795, 776, 709, 662, 629 cm$^{-1}$. UV (CH$_2$Cl$_2$): $\lambda_{max}$ (ε)=242 (10,700), 351 nm (31,900 l.mol$^{-1}$ cm$^{-1}$). HRMS (EI): calculated for C$_9$H$_5$O$_2$BrS: 255.9194; found 255.9202; C$_9$H$_5$O$_2$BrS (257.10): C 42.04, H 1.96; found C 42.16, H 2.04.

4-Phenyl-(Z)-5-(thiophene-3-ylmethylene)furan-2-(5H)-one (8b)

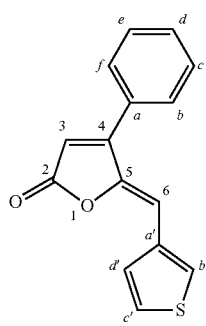

In a Schlenk tube, under inert atmosphere, containing 6b (101 mg, 0.39 mmol), phenylboronic acid (70 mg, 0.58 mmol), K$_3$PO$_4$ (123 mg, 0.58 mmol), S-Phos 10 (3 mg, 2 mol %) and Pd(OAc)$_2$ (8 mg, 3 mol %), toluene (3 ml) is added. The Schlenk tube is then stoppered with a septum, and the reaction medium is stirred for 24 h at 110° C. After returning to room temperature, CH$_2$Cl$_2$ (30 ml) is added to the reaction medium which then is filtered on a fritted disc containing a small amount of silica. The solvents are evaporated with a rotary evaporator and the residue is chromatographed on silica, with a CH$_2$Cl$_2$/pentane mixture (50/50) as eluent. A yellow solid is obtained with 66% yield (66 mg, 0.26 mmol).

R$_f$=0.65 (CH$_2$Cl$_2$/pentane, 60:40), MP 70-72° C. $^1$H-NMR (CDCl$_3$): δ=6.19 (d, 1H, J=0.6 Hz, 3-H), 6.28 (s, 1H, 6-H), 7.35 (dd, 1H, J=5.1 Hz, J=3.0 Hz, d'-H), 7.48-7.57 (m, 6H, c'-H, b-H, c-H, d-H, e-H, f-H), 7.77 (dd, 1H, J=2.9 Hz, J=0.6 Hz, b'-H) ppm. $^{13}$C-NMR (CDCl$_3$): δ=107.9 (C-6), 114.3 (C-3), 126.2, 128.4, 128.7, 129.0, 129.1, 130.4, 134.4, 147.0 (C-5), 158.3 (C-4), 168.6 (C-2) ppm. IR (KBr): υ=3101, 1759 (C=O), 1644, 1570, 1514, 1489, 1414, 1348, 1248, 1196, 1085, 937, 917, 875, 837, 812, 771, 703, 665, 636 cm$^{-1}$. UV (CH$_2$Cl$_2$): λ$_{max}$ (ε)=228 (11,400), 351 nm (17,000 l.mol$^{-1}$ cm$^{-1}$). HRMS (EI): calculated for C$_{15}$H$_{10}$O$_2$S: 254.0401; found 254.0374; C$_{15}$H$_{10}$O$_2$S (254.04): C 70.84, H 3.96; found C 70.68, H 4.03.

(Z)-5-(Bromophenylmethylene)furan-2-(5H)-one (7a)

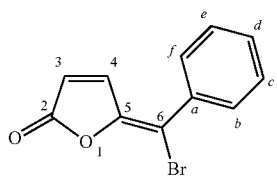 [SMILES: O=C1C=C/C(=C(/Br)c2ccccc2)O1]

In a Schlenk tube, under inert atmosphere, containing 3 (180 mg, 0.71 mmol), phenylboronic acid (129 mg, 1.06 mmol), Na$_2$CO$_3$ (150 mg, 1.42 mmol) and Pd(PPh$_3$)$_4$ (24 mg, 3 mol %), toluene (3 ml), H$_2$O (1.5 ml) and ethanol (0.9 ml) are added. The Schlenk tube is then stoppered with a septum, and the reaction medium is stirred for 24 h at room temperature. Water (30 ml) is then added to the reaction medium. It is extracted with ether (3×20 ml). The combined organic phases are washed with NaCl saturated water solution and dried on Na$_2$SO$_4$. The solvents are evaporated with a rotary evaporator, and the residue is chromatographed on silica with an Et$_2$O/pentane mixture (25/75) as eluent. A cream-white solid is obtained with 48% yield (94 mg, 0.37 mmol).

R$_f$=0.45 (Et$_2$O/pentane, 75:25), MP<50° C. $^1$H-NMR (CDCl$_3$): δ=6.32 (d, 1H, J=5.4 Hz, 3-H), 7.43-7.46 (m, 6H, H$_4$, ArH) ppm. $^{13}$C-NMR (CDCl$_3$): ε=110.9 (C-6), 120.8 (C-3), 128.8, 130.1, 130.2, 135.4, 140.9 (C-4), 149.1 (C-5), 168.5 (C-2) ppm. IR (KBr): υ=3135, 3096, 3031, 1788 (C=O), 1774 (C=O), 1628, 1612, 1548, 1540, 1486, 1443, 1230, 1106, 1072, 956, 920, 901, 863, 860, 817, 806, 749, 711, 689, 625, 535 cm$^{-1}$. UV (CH$_2$Cl$_2$): λ$_{max}$ (ε)=321 nm (20,400 l.mol$^{-1}$cm$^{-1}$). HRMS (EI): calculated for BrC$_{11}$H$_7$O$_2$: 249.9630; found 249.9628; BrC$_{11}$H$_7$O$_2$ (251.08): C 52.62, H 2.81; found C 52.61, H 2.90.

(Z)-5-(phenylthiophene-3-ylmethylene)furan-2-(5H)-one (9a)

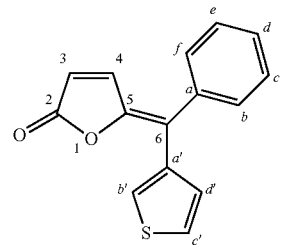

In a Schlenk tube, under inert atmosphere, containing 7a (480 mg, 1.91 mmol), thiophene-3-boronic acid (366 mg, 2.86 mmol), Na$_2$CO$_3$ (404 mg, 3.82 mmol) and Pd(PPh$_3$)$_4$ (66 mg, 3 mol %), toluene (10 ml), H$_2$O (5 ml) and ethanol (2.5 ml) are added. The Schlenk tube is then stoppered with a septum, and the reaction medium carried at 80° C. for 2.5 h. After returning to room temperature, water (50 ml) is added to the reaction medium. It is extracted with ether (3×20 ml). The combined organic phases are washed with 50 ml NaCl saturated water solution and dried on Na$_2$SO$_4$. The solvents are evaporated with a rotary evaporator and the residue is chromatographed on silica with a CH$_2$Cl$_2$/pentane mixture (70/30) as eluent. A pale yellow solid is obtained with 48% yield (233 mg, 0.92 mmol).

R$_f$=0.50 (CH$_2$Cl$_2$/pentane, 70:30). $^1$H-NMR (CDCl$_3$): δ=5.71 (d, 1H, J=5.4 Hz, 3-H), 7.28-7.37 (m, 3H, b'-H, c'-H, d'-H), 7.40-7.52 (m, 5H, 4-H, b-H, c-H, d-H, e-H, f-H) ppm. $^{13}$C-NMR (CDCl$_3$): δ=117.8 (C-3), 123.1 (C-6), 125.5, 128.4, 128.9, 129.5, 129.9, 130.8, 136.5, 137.7, 143.9 (C-4), 146.2 (C-5), 170.2 (C-2) ppm. IR: υ=3133, 3106, 3057, 2926, 1777 (C=O), 1752 (C=O), 1607, 1544, 1504, 1442, 1410, 1372, 1337, 1301, 1235, 1216, 1166, 1108, 1068, 1000, 979, 954, 892, 849, 807, 746, 712, 699, 682 cm$^{-1}$. UV (CH$_2$Cl$_2$): λ$_{max}$ (ε)=254 (9,000), 354 nm (19,000 l.mol$^{-1}$cm$^{-1}$). HRMS (EI): calculated for C$_{15}$H$_{10}$O$_2$S: 254.0401; found 254.0398; C$_{15}$H$_{10}$O$_2$S (254.30): C 70.84, H 3.96; found C 70.66, H 3.91.

(Z)-5-(Bromothiophene-3-ylmethylene)furan-2-(5H) one (7b)

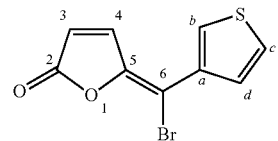 [SMILES: O=C1C=C/C(=C(/Br)c2ccsc2)O1]

In a Schlenk tube, under inert atmosphere, containing 2 (245 mg, 0.96 mmol), thiophene-3-boronic acid (185 mg, 1.44 mmol), Na$_2$CO$_3$ (204 mg, 1.93 mmol), and Pd(PPh$_3$)$_4$ (33 mg, 3 mol %), toluene (5 ml), H$_2$O (2.45 ml) and ethanol (1.22 ml) are added. The Schlenk tube is then stoppered with a septum, and the reaction medium is stirred for 3 days at room temperature. Water (30 ml) is then added to the reaction medium. It is extracted with ether (3×20 ml). The combined organic phases are washed with 30 ml NaCl saturated water solution and dried on Na$_2$SO$_4$. The solvents are evaporated with a rotary evaporator and the residue is chromatographed on silica with an Et$_2$O/pentane mixture (35/65) as eluent. A pale yellow solid is obtained with 40% yield (99 mg, 0.38 mmol).

R$_f$=0.65 (Et$_2$O/pentane, 75:25), MP 65-67° C. $^1$H-NMR (CDCl$_3$): δ=6.33 (d, 1H, J=5.6 Hz, 3-H), 7.25 (dd, 1H, J=6.4 Hz, J=1.3 Hz, d-H), 7.43 (dd, 1H, J=4.9 Hz, J=3.1 Hz, c-H), 7.47 (dd, 1H, J=2.9 Hz, J=1.4 Hz, b-H), 7.59 (d, 1H, J=5.4 Hz, 4-H) ppm. $^{13}$C-NMR (CDCl$_3$): δ=105.2 (C-6), 120.6 (C-3), 127.1, 127.4, 128.6, 136.0, 140.6 (C-4), 148.9 (C-5), 168.4 (C-2) ppm. IR (KBr): υ=3135, 3107, 2916, 2848, 1781 (C=O), 1756 (C=O), 1621, 1546, 1512, 1410, 1366, 1335, 1261, 1230, 1181, 1108, 1070, 991, 928, 890, 839, 807, 781, 748, 696 cm$^{-1}$. UV (CH$_2$Cl$_2$): λ$_{max}$ (ε)=255 (9,100), 334 nm (20,400 l.mol$^{-1}$cm$^{-1}$). HRMS (EI): calculated for BrC$_9$H$_5$O$_2$S: 255.9194; found 255.9202; BrC$_9$H$_5$O$_2$S (257.10): C 42.04, H 1.96; found C 42.12, H 2.02.

(E)-5-(phenylthiophene-3-ylmethylene)furan-2-(5H)-one (9b)

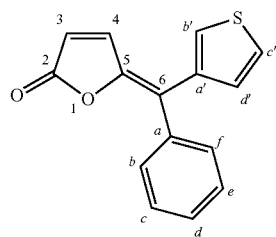 [SMILES: O=C1C=C/C(=C(/c2ccccc2)c2ccsc2)O1]

In a Schlenk tube, under inert atmosphere, containing 7b (76 mg, 0.29 mmol), phenylboronic acid (54 mg, 0.44 mmol), Na$_2$CO$_3$ (62 mg, 0.59 mmol) and Pd(PPh$_3$)$_4$ (13 mg, 3 mol %), toluene (2 ml), H$_2$O (1 ml) and ethanol (0.5 ml) are added. The Schlenk tube is then stoppered with a septum, and the reaction medium carried at 80° C. for 5 h. After returning to room temperature, water (5 ml) is added to the reaction medium. It is extracted with ether (3×15 ml). The combined organic phases are washed with NaCl saturated water solution and dried on Na$_2$SO$_4$. The solvents are evaporated with a rotary evaporator and the residue is chromatographed on silica with an Et$_2$O/pentane mixture (30/70) as eluent. A yellow oil is obtained with 42% yield (31 mg, 0.12 mmol).

R$_f$=0.39 (Et$_2$O/pentane, 25:75), MP 118-119° C. $^1$H-NMR (CDCl$_3$): δ=6.22 (d, 1H, J=5.6 Hz, H-3), 6.98 (dd, 1H, J=4.9 Hz, J=1.3 Hz, d'-H), 7.31 (dd, 1H, J=3.1 Hz, J=1.3 Hz, b'-H), 7.35-7.42 (m, 4H, c'-H and b-H or c-H or d-H or e-H or f-H), 7.49-7.53 (m, 2H, b-H or c-H or d-H or e-H or f-H), 7.62 (d, 1H, J=5.6 Hz, 4-H) ppm. $^{13}$C-NMR (CDCl$_3$): δ=118.5 (C-3), 123.6 (C-6), 126.3, 127.2, 128.2, 129.2, 129.8, 130.9, 136.1, 137.6, 143.5 (C-4), 147.2 (C-5), 170.4 (C-2) ppm. IR 3132, 3102, 3049, 1771 (C=O), 1755 (C=O), 1617, 1573, 1540, 1489, 1444, 1416, 1233, 1166, 1103, 1084, 990, 897, 874, 850, 816, 792, 750, 694, 671, 656, 613 cm$^{-1}$. UV (CH$_2$Cl$_2$): λ$_{max}$ (ε)=250 (10,900), 352 nm (21,400 l.mol$^{-1}$cm$^{-1}$). HRMS (EI): calculated for C$_{15}$H$_{10}$O$_2$S: 254.0401; found 254.0398; C$_{15}$H$_{10}$O$_2$S (254.31): C 70.84, H 3.96; found C 70.71, H 3.99.

5-(9H-Fluoren-9-ylidene)furan-2-(5H)-one (11)

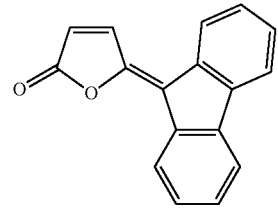

Rf (EtOAc/cyclohexane 1:2)=0.44

HRMS calc. M$^+$246.0681, found 246.0667.

δ$_H$ (270 MHz, CDCl$_3$): 8.36-8.34 (2H, m, H aromatic), 7.73-7.68 (3H, m, 2H aromatic and 1H olefinic), 7.39-7.25 (4H, m, H aromatic), 6.48 (1H, d, J=5.38 Hz, 1H olefinic).

δ$_C$ (67.80 MHz, CDCl$_3$): 170.65, 147.60, 141.80, 140.80, 140.55, 135.85, 135.44, 129.93, 129.39, 128.38, 128.10, 127.36, 123.70, 120.79, 120.58, 119.79.

The present inventors showed that all of the methylene furanone derivatives of general formula (I), as claimed in the present invention, have photoprotecting and antioxidant activity.

It is known that the skin constitutes a direct target of numerous environmental agents including ultraviolet rays A and B, UVC being stopped by the ozone layer.

UVB rays (5% of terrestrial UV energy) reach the cutaneous epidermis while UVA rays (95% of terrestrial energy) penetrate deeper since they reach the cutaneous dermis. The biological consequences this UV stress are described as an increase in the inflammatory response and the development of an erythema, a modulation of the immune response and, later, premature ageing and the promotion of skin cancers.

UVA and UVB, by different access routes, disrupt genome stability. UVB are primarily absorbed by the DNA molecule and predominantly generate inhibiting damage such as cyclobutane pyrimidine dimers and 6-4-pyrimidine-pyrimidone pyrimidine dimers. These photoproducts are repaired specifically by cell defence systems, such as repair by nucleotide excision.

UVA are primarily absorbed by molecules other than DNA, namely chromophores, thus generating the production of oxygenated free radicals capable of attacking DNA and creating damage, such as breaks in strands, directly or due to labile alkali sites. The cell also has specific repair systems for these lesions on the DNA.

Today, it is widely accepted that UVA and UVB rays can be mutagenic and constitute potential promoters of cutaneous photocarcinogenesis. It thus seems imperative to protect the skin from the deleterious effects of ultraviolet rays by topical sun screens possessing powerful filters against UVA and/or UVB.

The methylene furanone derivatives of general formula (I) of the present invention were thus evaluated in order to determine their photoprotecting capacity by determination of their UV absorption characteristics: molar extinction coefficient ε, critical wavelength (λc) and UVA/UVB ratio.

The results obtained show that the molar extinction coefficients of the inventive compounds range from 12,300 l.mol$^{-1}$.cm$^{-1}$ to 31,900 l.mol$^{-1}$.cm$^{-1}$ including a vast majority above 20,000 l.mol$^{-1}$.cm$^{-1}$, which is certainly in the range of products used in the cosmetics industry. Putting aside 4b and 4c, whose maximum is in UVB, they all have a maximum absorption in UVA. The critical wavelength confirms this observation; indeed, it is higher than 370 nm for most of the molecules. The UVA/UVB ratio indicates that these are broad filters (R≥1.5), which cover UVA well but also part of UVB.

By gathering all this information and by comparing the shape of the UV absorption spectra, these molecules can be classified in three categories:

Strict UVA Category (see FIG. 1 in Appendix)
(Molecules Absorbing Only in UVA):
5a, 4c, 6b, 9b, 9a, 5b, 4d, 5e, 5d
λc>370 nm
3<R<6.5

In this category only 5a and 6b have a λc<370 (respectively 367 nm and 355 nm). All these molecules absorb in long UVA (340-400 nm), which is interesting because few commercial filters, currently, cover this range. It should also be noted that the compounds substituted by donor groups absorb in general at higher wavelengths.

Figure 2:
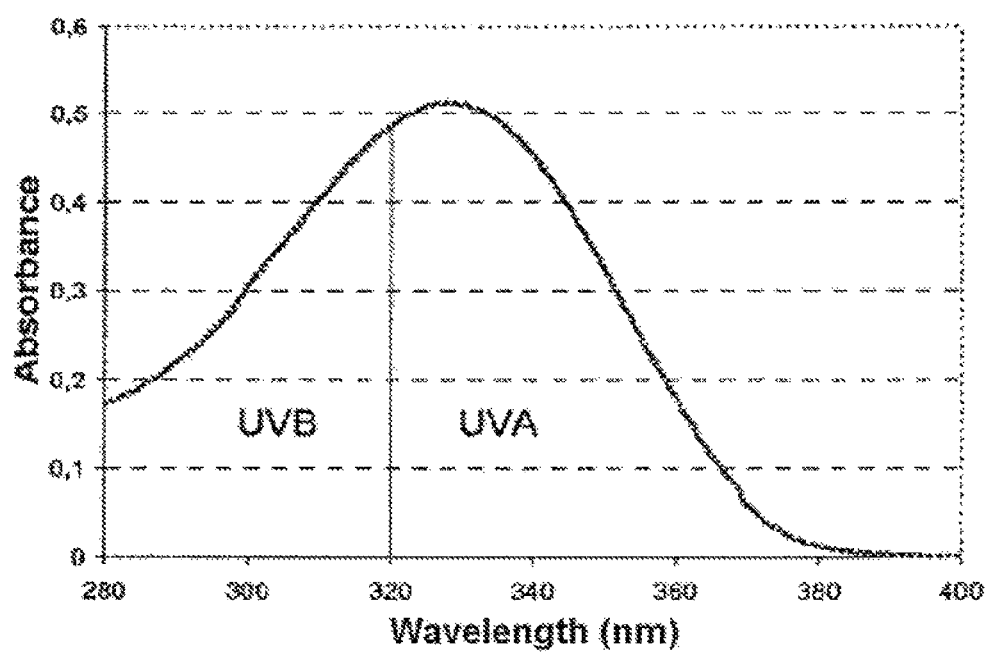
FIG. 2 depicts a graph that illustrates molecules absorbing predominatly in UVA and a minority in UVB (UVA extended towards B Category)

UVA Extended Towards B Category (See FIG. 2 in Appendix)
(Molecules Absorbing Predominantly in UVA and a Minority in UVB):
7a, 5f, 7b, 4a, 8a, 6a, 4f, 8b, 5c
λc<370 nm
1.5<r<3

As indicated on the absorption spectrum above as an example, these molecules have a maximum absorption in UVA but also cover a large part of UVB. This is confirmed by the value of the UVA/UVB ratio, which is between 1.5 and 3 for 8 of these 9 compounds. A majority of these molecules also absorb in long UVA wavelengths (4a, 8a, 6a, 4f, 8b, 5c).

Figure 3:
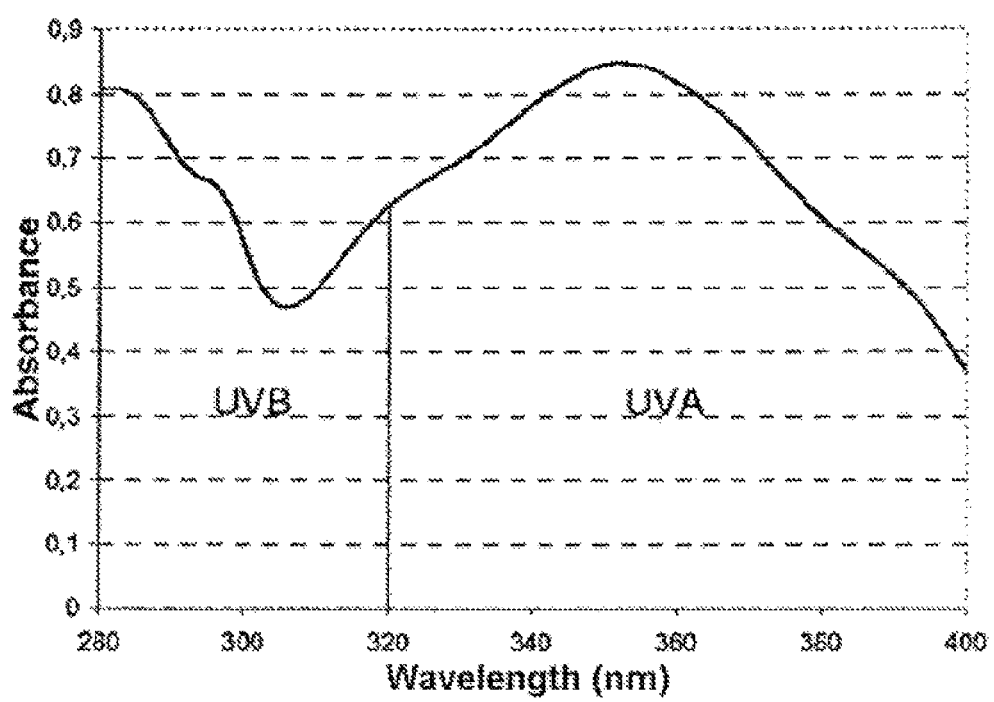
FIG. 3 depicts a graph that illustrates molecules having a maximum absorption in UVA and UVB (UVA+B Category).

UVA+B Category (see FIG. 3 in Appendix)
(Molecules Having a Maximum of Absorption in UVA and UVB):
4b, 4c
λc>370 nm
r=1.9 and 3.2

These two molecules also have advantageous properties, since they absorb in UVA and UVB, and more particularly 4c with a desirable molar extinction coefficient of 22,000 l. $mol^{-1}.cm^{-1}$.

Photostability

Tests of photostability were carried out on seven molecules, namely 4d, 5a, 5b, 5d, 5e and 9a (strict UVA) as well as 5f (UVA extended towards B):

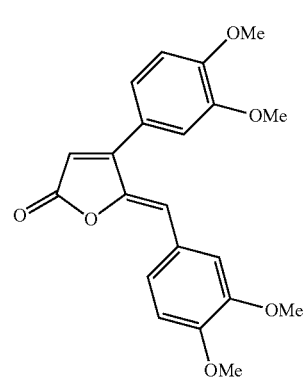
4d

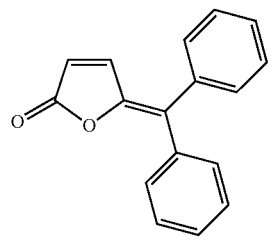
5a

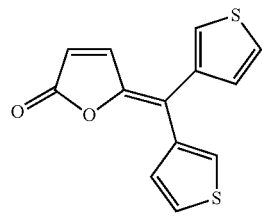
5b

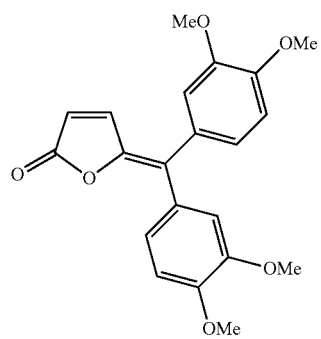
5d

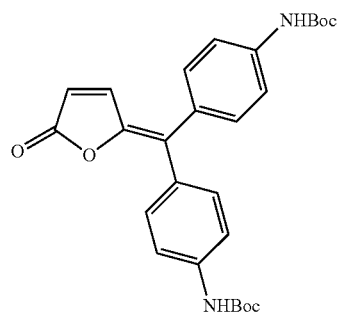
5e

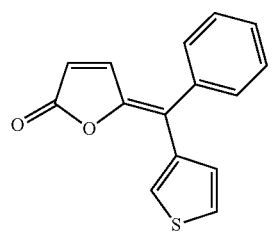
9a

5f

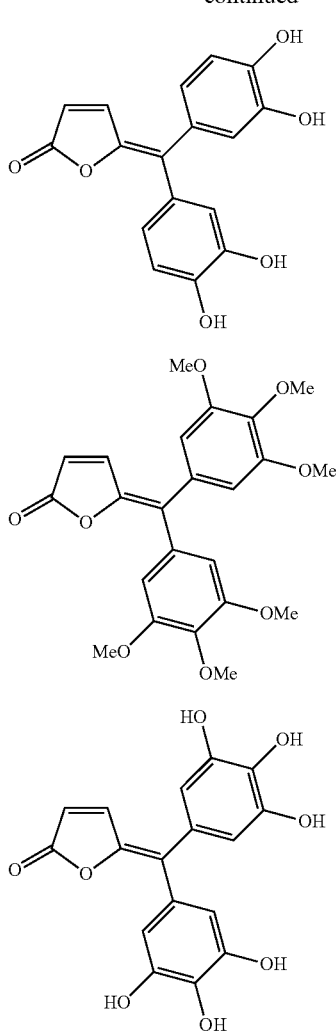

For this study it was decided to irradiate samples, in powder form or in solution in ethanol, with 10 MED (minimal erythema dose: minimum amount of solar radiation causing the appearance of sunburn). The evaluation of degradation is estimated by the shape of the UV absorption spectra before and after irradiation.

| Molecules | In solution | Powder |
|---|---|---|
| 4d | moderately stable | stable |
| 5a | stable | stable |
| 5b | stable | stable |
| 5d | stable | not stable |
| 5e | stable | stable |
| 9a | stable | stable |
| 5f | stable | stable |

Evaluation of Stability of Methylene Furanone Derivatives Irradiated in Suntest.

The results presented in the table above indicate that five of the seven compounds tested have very good photostability. Only 4d is moderately stable in solution, and 5d is completely unstable in powder form.

Study of Antioxidant Capacity of the Molecules

The antioxidant capacity of 10 molecules was measured by trapping the superoxide anion: 5d, 9a, 5b, 5a, 5e, 4d, 5f, 5g, 5h, 5j.

The method consists in generating free radicals by a photochemical signal. Oxidation intensity is 1000 times higher than that obtained in normal conditions.

Thus, the superoxide radical ($O_2$—) is generated by a photochemical reaction:

$$L + h\nu(UV) + O_2 \rightarrow L^*O_2 \rightarrow L^+ + O_2-$$

L*: luminol in an excited state
L⁺: luminol radical

Detection is done by chemiluminescence. It enables the evaluation of water-soluble and fat-soluble antioxidant molecules or extracts.

Part of the superoxide anions are quenched by antioxidants. The remaining free radicals are quantified by chemiluminescence.

$$L^+ + O_2^- \rightarrow N_2 + AP^{*2-} \rightarrow AP^{2-} + h\nu \text{ (luminescence)}$$

$AP^{*2-}$: aminophthalate in an excited state

The results are expressed respectively in equivalent quantity of vitamin C or Trolox (6-hydroxy-2,5,7,8-tetramethyl-chroman-2-carboxylic acid). Sensitivity is on the order of a nanomole.

| Name | Conditions | Photosensitising | Antioxidant |
|---|---|---|---|
| White | 100% $O_2^-$ generated | + | – |
| Standards | Standard range: from 1 nmol to 3 nmol | + | Vitamin C or Trolox |
| Test | +/– $O_2^-$ generated | + | Molecule x |

The analysis of the results depends on two criteria: shape of the curve and numerical value given by the software.

The results will be expressed in μg of sample necessary to obtain an activity equivalent to the activity detected for 1 μg of the standard (ascorbic acid or Trolox).

| Products | μg of sample for 1 μg of Trolox |
|---|---|
| Vitamin C | 0.451 |
| Trolox | 1.067 |
| Butylhydroxyanisole (BHA) | 2.650 |
| Bilirubin | 4.18 |
| Butylhydroxytoluene (BHT) | 7.26 |
| Idebenone | 10.10 |
| α-tocopherol-acetate | 140 |
| Cysteine | 698 |
| Albumin | 3069 |
| Lipoic acid | NEGATIVE |

| Sample | ACL μg of sample for 1 μg of Trolox |
|---|---|
| 5d | 12.7 |
| 9a | 21.6 |
| 5b | 28.0 |
| 5a | 43.0 |
| 5e | 46.3 |
| 4d | 50.2 |
| 5f | 88.3 |

-continued

| Sample | ACL µg of sample for 1 µg of Trolox |
|---|---|
| 5g | 0.03 |
| 5h | 30 |
| 5i | 1.5 |

Study of Depigmentation Capacity of (poly)hydroxylated Methylene Furanone Compounds:

Target:

Tyrosinase is a limiting enzyme in melanogenesis. It belongs to the family of oxidoreductases. It notably has the monophenol monooxygenase and polyphenol oxidase functions. It is synthesised in melanocytes. It is activated during its migration towards keratinocytes via melanosomes. It transforms tyrosine into DOPA and then dopaquinone, which eventually leads to polymerization and pigment production.

Principle:

The monophenol monooxygenase function is measured in this test. Tyrosinase activity (MPMO in the strict sense) is measured.

The substrate: L-tyrosine is transformed into L-DOPA. The enzymatic reaction is stopped at this stage. The DOPA produced is determined by an external calibration (0.005 mM to 0.1 mM). The final result is a percentage of inhibition compared to maximum activity without inhibitor or extract.

Result:

For a 50 quantity, compound 5g inhibits 65.93% of MPMO enzyme activity.

CONCLUSION

Tests based on UV absorption data showed that these novel methylene furanone derivatives absorb predominantly in UVA with desirable molar extinction coefficients. The shape of the spectra made it possible to classify them in three categories: strict UVA, UVA extended towards B, and UVA+B. Gem-disubstituted methylene furanones are predominantly present in the strict OVA category. The introduction of aromatics carrying attractor aminocarbamate or methoxy groups appear responsible for a bathochromic effect because some molecules absorb in the long UVA range towards 380 nm.

The tests carried out on these lactones indicate that the majority of these molecules are photostable and that they are also good antioxidants. These compounds thus have advantageous photoprotecting and antioxidant capacities which justify their use in dermocosmetic compositions.

The MPMO inhibition enzyme test showed the depigmenting properties of (poly)hydroxylated methylene furanone compounds.

The invention claimed is:

1. A compound of general formula (I):

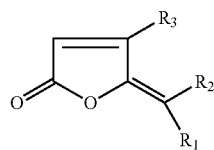

(I)

in their (E) or (Z) isomer forms, pure or in mixture, wherein
R3 represents hydrogen,
$R_1$ and $R_2$, are identical and represent
a phenyl radical substituted by one or more of the following radicals
($C_{1-5}$) alkyl, ($C_{1-4}$) alkoxy,
hydroxy,
methylthio,
halogen, or
an amino group optionally substituted by a ($C_{1-4}$) alkyl or ($C_{1-4}$) alkoxycarbonyl radical,
a thiophenyl radical,
a thionaphthenyl radical,
a thiazolyl radical,
a pyridinyl radical,
a benzomorpholinyl radical, or
a naphthyl radical
and with the proviso that $R_1$ and $R_2$ do not simultaneously represent a paramethoxyphenyl radical.

2. The compound of general formula (I) according to claim 1, wherein:
$R_3$ represents hydrogen
$R_1$ and $R_2$ are identical and represent
a phenyl radical substituted by one or more of the following radicals
($C_{1-4}$) alkoxy,
hydroxy,
a thiophenyl radical,
and with the proviso that $R_1$ and $R_2$ do not simultaneously represent a paramethoxyphenyl radical.

3. The compound of general formula (I) according to claim 1, wherein:
$R_3$ represents hydrogen
$R_1$ and $R_2$ are identical and represent
a phenyl radical substituted by one or more hydroxy radicals.

4. The compound of general formula (I) according to claim 1, in their (E) or (Z) isomer forms, pure or in mixture, wherein it is selected from the group consisting of:
5-(bis(3,4-dimethoxyphenyl)methylene)furan-2(5H)-one;
5-(dithiophene-3-ylmethylene)furan-2(5H)-one;
5-bis(tert-butyl-4-hydroxyphenylcarbamate)furan-2(5H)-one;
(Z)-5-(3,4-dimethoxyphenylmethylene)-4-(3,4-dimethoxyphenylmethylene)furan-2(5H)-one;
5-(bis(2-fluorophenyl)methylene)furan-2(5H)-one;
5-(bis(4-(methylthio)phenyl)methylene)furan-2(5H)-one;
5-(bis(4-(dimethylamino)phenyl)methylene)furan-2(5H)-one;
5-(bis(4-methyl-3,4-dihydro-2H-benzo[b][1,4]oxazin-7-yl)methylene)furan-2(5H)-one;
5-(dithiazol-2-ylmethylene)furan-2(5H)-one;
5-(bis(4-fluorophenyl)methylene)furan-2(5H)-one;
5-(bis(4-hydroxy-3,5-dimethylphenyl)methylene)furan-2(5H)-one;
5-(bis(3,4,5-trihydroxyphenyl)methylene)furan-2(5H)-one;
5-(bis(3,4-dihydroxyphenyl)methylene)furan-2(5H)-one;
5-(bis(4-hydroxy-3-methoxyphenyl)methylene)furan-2(5H)-one;
5-(bis(4-hydroxy-3,5-dimethoxyphenyl)methylene)furan-2(5H)-one;
5-(bis(4-hydroxyphenyl)methylene)furan-2(5H)-one;
5-(bis(2,4-dimethoxyphenyl)methylene)furan-2(5H)-one; and
5-(bis(2,4-dihydroxyphenyl)methylene)furan-2(5H)-one.

5. A method for photoprotecting the skin against the sun, comprising;
administering to a subject the compound of formula (I) according to claim 1, wherein
$R_3$ represents hydrogen, and
$R_1$ and $R_2$ are identical or different and represent
a phenyl radical optionally substituted by one or more of the following radicals
$(C_{1-5})$ alkyl, $(C_{1-4})$ alkoxy,
hydroxy,
methylthio,
halogen, or
an amino group optionally substituted by a $(C_{1-4})$ alkyl or $(C_{1-4})$ alkoxycarbonyl radical,
a thiophenyl radical,
a thionaplithenyl radical,
a thiazoiyl radical,
a pridinyl radical,
a benzomorpholinyl radical,
a naphthyl radical, or
$R_1$ and $R_2$ are bonded together and represent a fluorenyl radical,
with the proviso that $R_1$ and $R_2$ do not simultaneously represent a paramethoxphenyl radical, and wherein the compound of formula (I) is used as a photoprotecting agent.

6. A method for antioxidant protection of skin against UVA and/or UVB comprising administering on the skin a compound of formula (I) according to claim 1, wherein
$R_3$ represents hydrogen, and
$R_1$ and $R_2$ are identical or different and represent
a phenyl radical optionally substituted by one or more of the following radicals
$(C_{1-5})$ alkyl, $(C_{1-4})$ alkoxy,
hydroxy,
methylthio,
halogen, or
an amino group optionally substituted by a $(C_{1-4})$ alkyl or $(C_{1-4})$ alkoxycarbonyl radical,
a thiophenyl radical,
a thionaphthenyl radical,
a thiazolyl radical,
a pyridinyl radical,
a benzomorpholinyl radical,
a naphthyl radical,
$R_1$ and $R_2$ are bonded together and represent a fluorenyl radical, and
with the proviso that $R_1$ and $R_2$ do not simultaneously represent a paramethoxyphenyl radical, and wherein the compound of formula (I) is used as an antioxidant.

7. A method for depigmenting skin comprising administering to a subject a compound of formula (I) according to claim 1, wherein
$R_3$ represents hydrogen, and
$R_1$ and $R_2$ are identical and represent phenyl radical substituted by one or more hydroxyl radicals.

8. A composition comprising a cosmetically acceptable excipient and the compound of formula (I) according to claim 1.

9. The composition according to clam 8, wherein it is provided as a cream, gel or spray.

10. A method for preparing a compound of general formula (I):

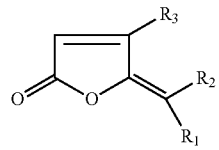

wherein
$R_3$ represents hydrogen,
$R_1$ and $R_2$ are identical and represent
a phenyl radical substituted by one or more of the following radicals
$(C_{1-5})$ alkyl, $(C_{1-4})$ alkoxy,
hydroxy,
methylthio,
halogen, or
an amino group optionally substituted by a $(C_{1-4})$ alkyl or $(C_{1-4})$ alkoxycarbonyl radical,
a thiophenyl radical,
a thionaphthenyl radical,
a thiazolyl radical,
a pyridinyl radical,
a benzomorpholinyl radical, or
a naphthyl radical
and with the proviso that $R_1$ and $R_2$ do not simultaneously represent a paramethoxyphenyl radical, and
wherein it involves a Suzuki-Miyaura coupling reaction between a boronic acid and a compound of formula (II):

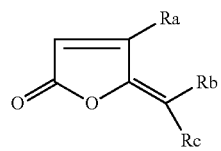

in its (E) or (Z) isomer forms, pure or in mixture,
wherein
Ra represents hydrogen and Rb and Rc represent a bromo radical, or
Rb represents hydrogen and Ra and Rc represent a bromo radical.

11. A method for preparing a compound of formula (I) such as defined in claim 1, wherein it involves a coupling reaction of 2-methoxy-furan with a ketone, followed by dehydration occurring either spontaneously in situ or with the help of a dehydration agent

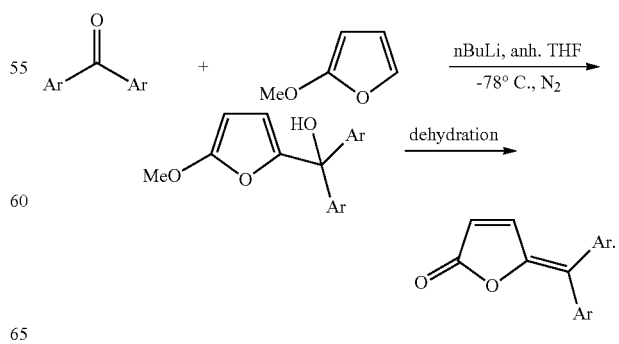

* * * * *